(12) United States Patent
Suzuki et al.

(10) Patent No.: US 11,052,174 B2
(45) Date of Patent: Jul. 6, 2021

(54) NERVE REGENERATION-INDUCING MATERIAL

(71) Applicants: Tazuke Kofukai, Osaka (JP); Mochida Pharmaceutical Co., Ltd., Tokyo (JP)

(72) Inventors: Yoshihisa Suzuki, Osaka (JP); Masao Tanihara, Nara (JP); Mitsuko Isaji, Tokyo (JP)

(73) Assignees: Tazuke Kofukai, Osaka (JP); Mochida Pharmaceutical Co., Ltd., Tokyo (JP)

( * ) Notice: Subject to any disclaimer, the term of this patent is extended or adjusted under 35 U.S.C. 154(b) by 110 days.

(21) Appl. No.: 16/083,600

(22) PCT Filed: Mar. 14, 2017

(86) PCT No.: PCT/JP2017/010274
§ 371 (c)(1),
(2) Date: Sep. 10, 2018

(87) PCT Pub. No.: WO2017/159700
PCT Pub. Date: Sep. 21, 2017

(65) Prior Publication Data
US 2019/0083678 A1    Mar. 21, 2019

(30) Foreign Application Priority Data
Mar. 14, 2016   (JP) .............................. JP2016-049955

(51) Int. Cl.
| *A61L 27/20* | (2006.01) |
| *A61L 27/18* | (2006.01) |
| *A61L 27/38* | (2006.01) |
| *A61L 27/58* | (2006.01) |
| *C08L 5/04*  | (2006.01) |
| *C08L 67/04* | (2006.01) |
| *C08K 5/3415* | (2006.01) |
| *A61L 27/48* | (2006.01) |

(52) U.S. Cl.
CPC .............. *A61L 27/20* (2013.01); *A61L 27/18* (2013.01); *A61L 27/383* (2013.01); *A61L 27/48* (2013.01); *A61L 27/58* (2013.01); *C08K 5/3415* (2013.01); *C08L 5/04* (2013.01); *C08L 67/04* (2013.01); *A61L 2430/32* (2013.01); *C08L 2203/02* (2013.01)

(58) Field of Classification Search
CPC .......... A61L 27/48; A61L 27/18; A61L 27/20; A61L 2430/32; A61L 27/383; A61L 27/58; C08L 5/04; C08L 67/04; C08L 2203/02; A61P 25/00; A61P 25/02; A61P 25/28; A61P 43/00; C08K 5/3415
See application file for complete search history.

(56) References Cited

U.S. PATENT DOCUMENTS

| 2005/0069525 A1 | 3/2005 | Mikael |
| 2007/0203564 A1 | 8/2007 | Rusk et al. |
| 2009/0075933 A1 | 3/2009 | Basu et al. |
| 2012/0238644 A1 | 9/2012 | Gong et al. |

FOREIGN PATENT DOCUMENTS

| CN | 1416918 A | 5/2003 | |
| CN | 105169486 A | 12/2015 | |
| JP | 2000-198738 A | 7/2000 | |
| JP | 2000198738 | * 7/2000 | ........... A61K 31/715 |
| JP | 2000-237294 A | 9/2000 | |
| JP | 2002-078792 A | 3/2002 | |
| JP | 2005-270237 A | 10/2005 | |
| JP | 4531887 B2 | 8/2010 | |
| JP | 2013-165884 A | 8/2013 | |

OTHER PUBLICATIONS

Kitahara et al. (J. Artif. Organs (1998) 1:22-27) (Year: 1998).*
Jeong et al. (Tissue Engineering and Regenerative Medicine, vol. 11, No. Suppl. 2, pp. 64-71 (2014) (Year: 2014).*
Hashimoto et al., "Peripheral nerve regeneration through alginate gel: analysis of early outgrowth and late increase in diameter of regenerating axons," Exp. Brain Res., 2002, 146:356-368.
Hashimoto et al., "Peripheral nerve regeneration using non-tubular alginate gel crosslinked with covalent bonds," Journal of Materials Science: Materials in Medicine, 2005, 16:503-509.
Hashimoto et al., "Novel Nerve Regeneration Materials Consisting of Alginate Gel Crosslinked with Covalent Bonds," J. Clinical and Experimental Medicine, 2005, 215(10):867-873, with English translation.
Hirai et al., "Evaluation of Regeneration of Transected Peripheral Nerve Using Sheet-like Artificial Material," Regenerative Medicine, 2017, 16(Suppl):331, O-45-5, with English translation.
Ishikawa et al., "New Findings on Nerve Healing Process of Peripheral Nerve Branches Using a Gel-like Artificial Nerve Material not having a Tubular Structure," 24th Research Council Meeting, 2015, 114, 01-041, with English translation.
Japanese Journal of Urology, 2006, 96(2):OP4-026.
Jeong et al., "Effect of Gamma Irradiation-Induced Degradation of Alginate Nanofibers for Tissue Engineering," Tissue Engineering and Regenerative Medicine, 2014, 11(Supp.2):64-71, with English abstract on first page.

(Continued)

*Primary Examiner* — Anna R Falkowitz
(74) *Attorney, Agent, or Firm* — Foley & Lardner LLP

(57) ABSTRACT

A non-tubular material for nerve regeneration induction, which can be used for the regeneration of a damaged part in a nerve, and which comprises: (A) a crosslinked form produced by crosslinking a low-endotoxin bioabsorbable polysaccharide having a carboxyl group in the molecule with at least one crosslinkable reagent selected from a compound represented by general formula (I) and a salt thereof via covalent bonds; and (B) a bioabsorbable polymer. $R^1HN-(CH_2)_n-NHR^2$ (I) [wherein $R^1$ and $R^2$ independently represent a hydrogen atom or a group represented by formula: $-COCH(NH_2)-(CH_2)_4-NH_2$, and n represents an integer of 2 to 18]. Thus, a medical material that can induce the regeneration of a damaged part in a nerve is provided.

14 Claims, 12 Drawing Sheets

(56) References Cited

OTHER PUBLICATIONS

Kataoka et al., "Alginate, a bioresorbable material derived from brown seaweed, enhances elongation of amputated axons of spinal cord in infant rats," Journal of Biomedical Materials Research, 2001, 54:373-384.

Matsuura et al., "Regeneration of Excised Pelvic Plexus Using Alginate or Chitosan Gel: 'Simply-Attaching' Method Without Sutures," Journal of Urology, May 24, 2005, 173(4:Supp):333, 1228.

Matsuura et al., "Cavernous Nerve Regeneration by Biodegradable Alginate Gel Sponge Sheet Placement without Sutures," Urology, 2006, 68(6):1366-1371.

Matsuura et al., "Regeneration of Penis Cavernous Nerves using Bioabsorbable Alginate Gel Sponge Sheet," J.J. Urology, 2006, 97(2):APP-089, with English translation.

Matsuura et al., "The Excised Cavernous Nerves Can Be Regenerated Simply by Sticking the Biodegradable Sheet Without Sutures," May 23, 2006, 175(4:Supp):421, 1307.

Matsuura et al., "Simple Penis Cavernous Nerve Regeneration Method Consisting only of Placement of Alginate Gel Sheet," J. J. Urology, 2007, 98(2):WS5-7, with English translation.

Miyamoto et al., "Rat Cavernous Nerve Reconstruction with CD133+ Cells Derived from Human Bone Marrow," Journal of Sexual Medicine, May 2014, 11(5):1148-1158.

Ohta et al., "Novel heparin/alginate gel combined with basic fibroblast growth factor promotes nerve regeneration in rat sciatic nerve," J. Biomed. Mater. Res. Pt. A, 2004, 71A(4):661-668.

Sufan et al., "Sciatic Nerve Regeneration Through Alginate With Tubulation or Nontubulation Repair in Cat," Journal of Neurotrauma, 2001, 18(3):329-338.

Suzuki et al., "Cat peripheral nerve regeneration across 50 mm gap repaired with a novel nerve guide composed of freeze-dried alginate gel," Neuroscience Letters, 1999, 259:75-78.

Suzuki et al., "Reconstruction of rat peripheral nerve gap without sutures using freeze-dried alginate gel," J. Biomed. Mater. Res., 2000, 49:528-533.

Suzuki et al., "Nontubulation Repair of Peripheral Nerve Gap Using Heparin/Alginate Gel Combined with b-FGF," PRS Global Open, 2016, 4(1):e600, 3 pages.

Tsuruta et al., "Preservation and Reconstruction of Cavernous Nerves During Radical Prostatectomy: Update," Japanese Journal of Urological Surgery, 2009, 22(2):133-138, with English translation.

Urology View, 2006, 4(4):74-79.

Wu et al., "Repair of Facial Nerve with Alginate Sponge Without Suturing: An Experimental Study in Cats," Scand. J. Plast. Reconstr. Surg. Hand Surg., 2002, 36:135-140.

* cited by examiner

Scale bars=50 μ m

Scale bars=50 μm

NERVE REGENERATION-INDUCING MATERIAL

CROSS-REFERENCE TO RELATED APPLICATIONS

This application is a National Stage application of PCT/JP2017/010274, filed Mar. 14, 2017, which claims priority from Japanese application JP 2016-049955, filed Mar. 14, 2016.

TECHNICAL FIELD

The present invention relates to a nerve regeneration-inducing material for regenerating nerve damage.

BACKGROUND ART

Examples of treatment methods performed for nerve damage caused by trauma or tumor resection and the like include nerve suture, in which two severed nerves are sutured directly, and autologous nerve graft, in which a healthy nerve of a patient per se is harvested and grafted to a damaged site. However, in methods in which nerves are sutured directly, tension may be generated that causes residual paraesthesia or pain, while autologous nerve graft has the shortcoming of requiring the sacrifice of a nerve of a healthy site while also resulting in the manifestation of pain and numbness at the location where the nerve was harvested.

Attempts to regenerate nerves by connecting the severed site of a peripheral nerve using a biocompatible material have been starting around the early 1980s, and there are several devices for nerve regeneration of linear nerve defects. For example, "Nerbridge™" is a nerve regeneration-inducing tube composed of polyglycolic acid and collagen. However, due to the cylindrical shape and the hard exterior material covering the collagen of the lumen, it is difficult to use Nerbridge for nerve regeneration at locations having a large range of movement such as joints of the fingers and toes or sites in the vicinity of joints as well as at locations requiring a three-dimensional curved shape. In addition, the procedure is complex since it is necessary to thread the end of a severed nerve inside the tube and immobilize in position by suturing, and since the inner diameter is fixed, it is always necessary to have tubes of multiple inner diameters on hand. In addition, Nerbridge cannot be used at nerve branches or nerve plexus defects, and nerves in which the stump of the severed nerve is clearly defined must be joined on a 1:1 basis. Another example of a tube that is joined to a nerve on a 1:1 basis is "NEURO-LAC (registered trademark)" composed of a copolymer of polylactic acid and ε-caprolactam.

A nerve regenerative effect on linear nerve defects has been disclosed that uses an alginic acid sponge produced by covalent bond crosslinking with ethylenediamine (Patent document 1).

A material obtained by covering alginate gel with polyglycolic acid formed into the shape of a tube followed by lyophilization has been disclosed to regenerate a 50 mm gap in the femoral portion of the sciatic nerve of a cat (Non-patent document 1). The alginate gel is indicated as being free of any differences in effects between tubular devices and non-tubular devices in terms of regeneration of cat sciatic nerve gap. The non-tubular device was installed by interposing the nerve gap between two sponges (Non-patent document 2). Technologies related to this have also been disclosed (Non-patent documents 3-6).

There are also examples of the use of an alginate sponge for a 2 mm gap in rat spinal cord (Non-patent document 7).

Regeneration of a 5 mm gap in the posterior branch of a facial nerve of a cat by using an alginic acid sponge has also been disclosed. However, the severed site of the nerve was not branched (Non-patent document 8).

There is also literature describing regeneration of a 2 mm gap in the cavernous nerve of a rat using an alginate gel sponge sheet (Non-patent documents 9-14). Since the severed site of the nerve is the cavernous nerve located 1 mm downstream from the pelvic ganglion, this is unlikely to be a branched nerve. With respect to regeneration of the cavernous nerve, although there are examples of the use of an alginate gel sponge sheet as a base material for administration of CD133-positive cells derived from human bone marrow, significant regenerative effects were not obtained with the alginate gel sponge sheet alone (Non-patent document 15). In addition, there are also examples of regeneration of an approximately 2 mm nerve defect of rat pelvic ganglion by affixing alginate gel thereto (Non-patent documents 16-17). Details of the alginate sheets used are not clarified in these literatures, and the effects thereof cannot be said to be adequate.

The alginate sponge used in the above-mentioned studies uses sodium alginate that has not been treated to have a low endotoxin level, and is not produced using low endotoxin sodium alginate.

In this manner, nearly all nerve regeneration that has been previously attempted using devices is for regeneration of linear nerve defects, and a practical material is not known that is able to promote regeneration of nerve branches and nerve plexus defects.

A biological tissue reinforcing material kit has been disclosed that contains a nonwoven fabric composed of a bioabsorbable material and sodium alginate (Patent document 2). However, the sodium alginate is used without being crosslinked and the objective of this material is not nerve regeneration.

There are several reports in the literature that examine the relationship between polymer materials such as polysaccharides and gamma rays or electron beams. Patent document 3 discloses a gel obtained by irradiating gel formed with hyaluronic acid alone with gamma rays, electron beam or plasma and the like. The gel consisting of hyaluronic acid alone is explained as referring to a self-crosslinking gel obtained without using a chemical crosslinking agent other than hyaluronic acid. Patent document 4 discloses an implant composed of a biodegradable polymer under chemical, heat or radiation conditions. Non-patent document 18 discloses a technology for controlling the rate of disintegration according to the dose of gamma radiation by irradiating alginate fibers for tissue engineering with gamma rays. In addition, literature relating to a nerve regeneration material using alginic acid describes that bioabsorbability of an alginate gel can be controlled according to the dose of gamma radiation (Non-patent document 19). However, the relationship between irradiation of materials with gamma rays or electron beam and nerve regeneration has yet to be clarified in detail.

PRIOR ART DOCUMENTS

Patent Documents

Patent document 1: Japanese Patent No. 4531887
Patent document 2: Japanese Patent Application Publication No. 2013-165884
Patent document 3: Japanese Patent Application Publication No. 2000-237294
Patent document 4: U.S. Patent Application Publication No. 2007/0203564 (Specification)

Non-Patent Documents

Non-patent document 1: Neuroscience Letters, 259 (1999) 75-78
Non-patent document 2: Journal of Neurotrauma, Vol. 18, No. 3 (2001) pp. 329-338
Non-patent document 3: J. Biomed. Mater. Res. (2000) 49: pp. 528-533
Non-patent document 4: Exp. Brain Res. (2002) 146: pp. 356-368
Non-patent document 5: J. Materials Science: Materials in Medicine, 16 (2005) pp. 503-509
Non-patent document 6: J. Biomed. Mater. Res. Pt. A: 71A(4) (2004) pp. 661-668
Non-patent document 7: Journal of Biomedical Materials Research, Vol. 54, pp. 373-384 (2001)
Non-patent document 8: Scandinavian Journal of Plastic and Reconstructive Surgery and Hand Surgery, 2002, 36: 135-140
Non-patent document 9: Urology 68: 1366-1371 (2006)
Non-patent document 10: The Japanese Journal of Urology (2006) Vol. 97, No. 2, APP-089, http://togodb.dbcls.jp/yokou_abstract/show/200601893130275
Non-patent document 11: The Journal of Urology (2006) Vol. 75, No. 4 Supplement, pp. 421, 1307
Non-patent document 12: The Japanese Journal of Urology (2007), Vol. 98, No. 2, http://togodb.dbcls.jp/yokou_abstract/show/200701846760209 WS5-6
Non-patent document 13: Urology View, Vol. 4, No. 4, pp. 74-79
Non-patent document 14: Japanese Journal of Urological Surgery (2009) 22(2), pp. 133-138
Non-patent document 15: J. Sex. Med. 2014, 11: pp. 1148-1158
Non-patent document 16: The Japanese Journal of Urology (2005) Vol. 96, No. 2, OP4-026, http://togodb.dbcls.jp/yokou_abstract/show/200501884320564
Non-patent document 17: The Journal of Urology (2005) Vol. 173, No. 4 Supplement, pp. 333, 1228
Non-patent document 18: Tissue Engineering and Regenerative Medicine, Vol. 11, Suppl. 2, pp. 64-71 (2014)
Non-patent document 19: Journal of Clinical and Experimental Medicine (2005), Vol. 215, No. 10, pp. 867-873

SUMMARY OF INVENTION

Problems to be Solved by the Invention

One object of the present invention is to provide a medical material capable of inducing regeneration of a damaged site of a branch of a nerve and/or nerve plexus.

Another object of the present invention is to provide a medical material that is highly effective in inducing nerve regeneration, safe and has superior biocompatibility, which can be applied to linear nerve damaged sites as well as a damaged site of a nerve branch and/or nerve plexus.

Still another object of the present invention is to provide a non-tubular nerve regeneration-inducing material that is capable of demonstrating a nerve regenerative effect even in cases of not suturing while provided with suitable strength that enables suturing and is easily applied to damage at various locations and in various forms.

Means for Solving the Problems

The present invention is based on the finding that a nerve regeneration-inducing material, which contains a xerogel-like crosslinked alginate produced by covalent bond crosslinking of low endotoxin sodium alginate with a compound, and/or salt thereof, represented by general formula (I) to be subsequently described, induced regeneration of a gap of a Y-shaped branch of sciatic nerve in a rat. Attempts to induce regeneration of a gap of a branch of the sciatic nerve using a device have not been made thus far. The induction of nerve regeneration by the nerve regeneration-inducing material of the present invention by connecting a single nerve stump with a plurality of nerve stumps in a gap of a branch of the sciatic nerve is a surprising finding that cannot be conceived of from previous findings.

In another aspect of the present invention, when a nerve regeneration-inducing material, which contains xerogel-like crosslinked alginic acid, produced by covalent bond crosslinking of low endotoxin sodium alginate with a compound, and/or salt thereof, represented by general formula (I) to be subsequently described, followed by irradiating with an electron beam was evaluated for the effect of inducing nerve regeneration of a nerve defect in a rat, the nerve regeneration-inducing material irradiated with an electron beam was found to enhance the effect of inducing nerve regeneration in comparison with that not irradiated with an electron beam. In addition, bioelimination (residual) time of the nerve regeneration-inducing material containing crosslinked alginate was found to influence the effect of inducing nerve regeneration, bioelimination time of the material was found to be able to be controlled by the dose of the electron beam or gamma rays, and the crosslinked form was found to have an elimination pattern desirable for nerve regeneration. In addition, a material for inducting nerve regeneration further containing a bioabsorbable polymer has fewer examples of insufficient regeneration in comparison with materials not containing a bioabsorbable polymer, and was suggested to have the possibility of stably regenerating nerve defects. This was an unexpected effect. In addition, a nerve regeneration-inducing material containing a bioabsorbable polymer was found to be able to be sutured as necessary, be able to inhibit deformation of the material during lyophilization, and have superior handling, thereby leading to completion of the present invention.

Namely, the present invention provides a nerve regeneration-inducing material as indicated below as a first aspect thereof.

(1-1) A nerve regeneration-inducing material used to regenerate a damaged site of a nerve branch and/or nerve plexus, the material containing: a crosslinked form obtained by covalent bond crosslinking a low endotoxin bioabsorbable polysaccharide having a carboxyl group within a molecule thereof with at least one type of crosslinking reagent selected from a compound represented by the following general formula (I) and a salt thereof:

$$R^1HN-(CH_2)_n-NHR^2 \qquad (I)$$

(wherein $R^1$ and $R^2$ respectively and independently represent a hydrogen atom or group represented by the formula: —COCH(NH$_2$)—(CH$_2$)$_4$—NH$_2$, and n represents an integer of 2 to 18).

(1-2) The nerve regeneration-inducing material according to (1-1), wherein the bioabsorbable polysaccharide having a carboxyl group in a molecule thereof is at least one type selected from the group consisting of alginic acid, an ester thereof and a salt thereof.

(1-3) The nerve regeneration-inducing material according to either of (1-1) or (1-2), wherein the crosslinking reagent is an N-hydroxysuccinimide salt of the compound represented by the above-mentioned general formula (I).

(1-4) The nerve regeneration-inducing material according to (1-3), wherein the N-hydroxysuccinimide salt of the compound represented by the above-mentioned general formula (I) is at least one type selected from the group consisting of a 2N-hydroxysuccinimide salt of diaminoethane, a 2N-hydroxysuccinimide salt of diaminohexane, a 4N-hydroxysuccinimide salt of N,N'-di(lysyl)-diaminoethane and a 3N-hydroxysuccinimide salt of N-(lysyl)-diaminohexane.

(1-5) The nerve regeneration-inducing material according to any one of (1-1) to (1-4), which is in the form of a xerogel.

(1-6) The nerve regeneration-inducing material according to any one of (1-1) to (1-5), wherein the bioabsorbable polysaccharide having a carboxyl group in a molecule thereof has an endotoxin content of 100 EU/g or less.

(1-7) The nerve regeneration-inducing material according to any one of (1-1) to (1-6), wherein the damaged site of a nerve branch and/or nerve plexus is present in at least one location selected from the group consisting of the prostate gland, arm, brain, spinal cord, face, neck, waist (lumbar region), sacrum, lumbosacrum, genitals, heart, abdominal cavity and within the intestinal wall.

(1-7a) The nerve regeneration-inducing material according to any one of (1-1) to (1-6), wherein the damaged site of a nerve branch and/or nerve plexus is present in at least one location selected from the group consisting of the prostate gland, bladder, cavernous body, arm, extremities, brain, spinal cord, face, neck, waist (lumbar region), sacrum, lumbosacrum, genitals, heart, abdominal cavity, lower abdomen, pelvis, within the thoracic cavity and within the intestinal wall.

(1-8) The nerve regeneration-inducing material according to any one of (1-1) to (1-7a), which is used to regenerate nerve damage accompanying lymph node dissection.

(1-9) A method for inducing regeneration of a nerve branch and/or nerve plexus in a subject in need of nerve regeneration, the method including a step for applying a nerve regeneration-inducing material, containing a crosslinked form obtained by covalent bond crosslinking a low endotoxin bioabsorbable polysaccharide having a carboxyl group within a molecule thereof with at least one type of crosslinking reagent selected from a compound represented by the above-mentioned general formula (I) and a salt thereof, to a damaged site of a nerve branch and/or nerve plexus.

(1-9a) A method for inducing regeneration of a damaged site of a nerve branch and/or nerve plexus in a subject in need of nerve regeneration, the method including a step for applying the nerve regeneration-inducing material according to any one of (1-1) to (1-8) to a damaged site of a nerve branch and/or nerve plexus.

(1-10) The low endotoxin bioabsorbable polysaccharide having a carboxyl group in a molecule thereof for use in regenerating a damaged site of a nerve branch and/or nerve plexus, which uses a nerve regeneration-inducing material containing a crosslinked form obtained by covalent bond crosslinking a low endotoxin bioabsorbable polysaccharide having a carboxyl group in a molecule thereof with a crosslinking reagent selected from a compound represented by the above-mentioned general formula (I) and a salt thereof.

(1-10a) The low endotoxin bioabsorbable polysaccharide having a carboxyl group in a molecule thereof for use in regenerating a damaged site of a nerve branch and/or nerve plexus, which uses the nerve regeneration-inducing material according to any one of (1-1) to (1-8).

(1-11) A use of the low endotoxin bioabsorbable polysaccharide having a carboxyl group in a molecule thereof and/or at least one type of crosslinking reagent selected from a compound represented by the above-mentioned general formula (I) and a salt thereof to produce the nerve regeneration-inducing material according to any one of (1-1) to (1-8), wherein the nerve regeneration-inducing material is used so as to regenerate a nerve by applying to a damaged site of a nerve branch and/or nerve plexus.

In addition, the present invention provides a nerve regeneration-inducing material as indicated below as a second aspect thereof.

(2-1) A nerve regeneration-inducing material containing a crosslinked form obtained by covalent bond crosslinking a low endotoxin bioabsorbable polysaccharide having a carboxyl group in a molecule thereof with at least one type of crosslinking reagent selected from a compound represented by the following general formula (I) and a salt thereof and irradiated with an electron beam and/or gamma rays:

$$R^1HN\text{—}(CH_2)_n\text{—}NHR^2 \quad (I)$$

(wherein $R^1$ and $R^2$ respectively and independently represent a hydrogen atom or group represented by the formula: —COCH(NH$_2$)—(CH$_2$)$_4$—NH$_2$, and n represents an integer of 2 to 18).

(2-2) The nerve regeneration-inducing material according to (2-1), wherein the bioabsorbable polysaccharide having a carboxyl group in a molecule thereof is at least one type selected from the group consisting of alginic acid, an ester thereof and a salt thereof.

(2-3) The nerve regeneration-inducing material according to either of (2-1) or (2-2), wherein the crosslinking reagent is an N-hydroxysuccinimide salt of a compound represented by the above-mentioned general formula (I).

(2-4) The nerve regeneration-inducing material according to (2-3), wherein the N-hydroxysuccinimide salt of a compound represented by the above-mentioned general formula (I) is at least one type selected from the group consisting of a 2N-hydroxysuccinimide salt of diaminoethane, a 2N-hydroxysuccinimide salt of diaminohexane, a 4N-hydroxysuccinimide salt of N,N'-di(lysyl)-diaminoethane and a 3N-hydroxysuccinimide salt of N-(lysyl)-diaminohexane.

(2-5) The nerve regeneration-inducing material according to any one of (2-1) to (2-4), which is in the form of a xerogel.

(2-6) The nerve regeneration-inducing material according to any one of (2-1) to (2-5), wherein the bioabsorbable polysaccharide having a carboxyl group in a molecule thereof has an endotoxin content of 100 EU/g or less.

(2-7) The nerve regeneration-inducing material according to any one of (2-1) to (2-6), wherein an electron beam and/or gamma rays are irradiated at an absorbed dose of 1 kGy to 100 kGy.

(2-8) The nerve regeneration-inducing material according to any one of (2-1) to (2-7), which is eliminated from the applied site in 7 days to 270 days.

(2-9) The nerve regeneration-inducing material according to any one of (2-1) to (2-8), further containing at least one type selected from the group consisting of polyglycolic acid, polylactic acid and a copolymer thereof.

(2-10) The nerve regeneration-inducing material according to any one of (2-1) to (2-9), which is used to regenerate a damaged site of a peripheral nerve and/or central nerve.

(2-11) The nerve regeneration-inducing material according to any one of (2-1) to (2-10), which is used to regenerate nerve damage accompanying lymph node dissection.

(2-12) The nerve regeneration-inducing material according to any one of (2-1) to (2-11), wherein the amount of time until elimination from an applied site in the body is short in comparison with a material not irradiated with an electron beam and/or gamma rays.

(2-13) A method for inducing regeneration of a damaged site of a nerve in a subject in need of regeneration of a damaged site of a nerve, the method including a step for applying the nerve regeneration-inducing material according to any one of (2-1) to (2-12) to the damaged site of a nerve.

(2-13a) The low endotoxin bioabsorbable polysaccharide having a carboxyl group in a molecule thereof for use in regenerating a damaged site of a nerve, which uses the nerve regeneration-inducing material according to any one of (2-1) to (2-12).

(2-13b) A use of the low endotoxin bioabsorbable polysaccharide having a carboxyl group in a molecule thereof and/or at least one type of crosslinking reagent selected from a compound represented by the above-mentioned general formula (I) and a salt thereof to produce the nerve regeneration-inducing material according to any one of (2-1) to (2-12), wherein the nerve regeneration-inducing material is used so as to regenerate a nerve by applying to a damaged site of a nerve.

(2-14) A method for adjusting the residual time in the body of a nerve regeneration-inducing material, the method including a step for irradiating the nerve regeneration-inducing material containing a crosslinked form, obtained by covalent bond crosslinking a low endotoxin bioabsorbable polysaccharide having a carboxyl group in a molecule thereof with at least one type of crosslinking reagent selected from a compound represented by the above-mentioned general formula (I) and a salt thereof, with an electron beam and/or gamma rays.

(2-15) A method for producing a nerve regeneration-inducing material, the method at least including a step for irradiating a material containing a crosslinked form, obtained by using a covalent bond crosslinking a low endotoxin bioabsorbable polysaccharide having a carboxyl group in a molecule thereof and at least one type of crosslinking reagent selected from a compound represented by the above-mentioned general formula (I) and a salt thereof, with an electron beam and/or gamma rays.

In addition, the present invention provides a nerve regeneration-inducing material as indicated below as a third aspect thereof.

(3-1) A nerve regeneration-inducing material, containing a crosslinked form obtained by covalent bond crosslinking at least one type selected from the group consisting of a low endotoxin alginic acid, ester thereof and salt thereof, in which the weight average molecular weight thereof as measured by GPC-MALS is 90,000 to 700,000, with at least one type of crosslinking reagent selected from a compound represented by the following general formula (I) and a salt thereof:

R¹HN—(CH₂)ₙ—NHR²                                    (I)

(wherein $R^1$ and $R^2$ respectively and independently represent a hydrogen atom or group represented by the formula: —COCH(NH₂)—(CH₂)₄—NH₂, and n represents an integer of 2 to 18).

(3-2) The nerve regeneration-inducing material according to (3-1), wherein the M/G ratio of at least one type selected from the group consisting of a low endotoxin alginic acid, ester thereof and salt thereof is 0.5 to 3.0.

(3-3) A method for regenerating a damaged site of a nerve in a subject in need of regeneration of a damaged site of a nerve, the method including a step for applying the nerve regeneration-inducing material according to either of (3-1) or (3-2) to the damaged site of a nerve.

(3-3b) The low endotoxin alginic acid, ester thereof or salt thereof for use in regenerating a damaged site of a nerve, which uses the nerve regeneration-inducing material according to either of (3-1) or (3-2).

(3-3c) A use of the low endotoxin alginic acid, ester thereof or salt thereof and/or at least one type of crosslinking reagent selected from a compound represented by the above-mentioned general formula (I) and a salt thereof to produce the nerve regeneration-inducing material according to either of (3-1) or (3-2), wherein the nerve regeneration-inducing material is used so as to regenerate a nerve by applying to a damaged site of a nerve.

In addition, the present invention provides a nerve regeneration-inducing material as indicated below as a fourth aspect thereof.

(4-1) A nerve regeneration-inducing material, containing a crosslinked form obtained by covalent bond crosslinking a low endotoxin bioabsorbable polysaccharide having a carboxyl group in a molecule thereof with at least one type of crosslinking reagent selected from a compound represented by the following general formula (I) and a salt thereof:

R¹HN—(CH₂)ₙ—NHR²                                    (I)

(wherein $R^1$ and $R^2$ respectively and independently represent a hydrogen atom or group represented by the formula: —COCH(NH₂)—(CH₂)₄—NH₂, and n represents an integer of 2 to 18).

(4-2) The nerve regeneration-inducing material according to (4-1), wherein the bioabsorbable polysaccharide having a carboxyl group in a molecule thereof is at least one type selected from the group consisting of alginic acid, an ester thereof and a salt thereof.

(4-3) The nerve regeneration-inducing material according to either of (4-1) or (4-2), wherein the crosslinking reagent is an N-hydroxysuccinimide salt of a compound represented by the above-mentioned general formula (I).

(4-4) The nerve regeneration-inducing material according to (4-3), wherein the N-hydroxysuccinimide salt of a compound represented by the above-mentioned general formula (I) is at least one type selected from the group consisting of a 2N-hydroxysuccinimide salt of diaminoethane, a 2N-hydroxysuccinimide salt of diaminohexane, a 4N-hydroxysuccinimide salt of N,N'-di(lysyl)-diaminoethane and a 3N-hydroxysuccinimide salt of N-(lysyl)-diaminohexane.

(4-5) The nerve regeneration-inducing material according to any one of (4-1) to (4-4), which is in the form of a xerogel.

(4-6) The nerve regeneration-inducing material according to any one of (4-1) to (4-5), wherein the weight average molecular weight as measured by GPC-MALS of at least one type selected from the group consisting of a low endotoxin alginic acid, ester thereof and salt thereof is 90,000 to 700,000.

(4-7) The nerve regeneration-inducing material according to any one of (4-1) to (4-6), wherein the M/G ratio of at least one type selected from the group consisting of a low endotoxin alginic acid, ester thereof and salt thereof is 0.5 to 3.0.

(4-8) The nerve regeneration-inducing material according to any one of (4-1) to (4-7), wherein the bioabsorbable polysaccharide having a carboxyl group in a molecule thereof has an endotoxin content of 100 EU/g or less.

(4-9) The nerve regeneration-inducing material according to any one of (4-1) to (4-8), further containing at least one type selected from the group consisting of polyglycolic acid, polylactic acid and a copolymer thereof.

(4-10) The nerve regeneration-inducing material according to any one of (4-1) to (4-9), which is eliminated from the applied site in 7 days to 270 days.

(4-11) The nerve regeneration-inducing material according to any one of (4-1) to (4-10), which is irradiated with an electron beam and/or gamma rays.

(4-12) The nerve regeneration-inducing material according to (4-11), wherein the electron beam and/or gamma rays are irradiated at an adsorbed dose of 1 kGy to 100 kGy.

(4-13) The nerve regeneration-inducing material according to any one of (4-1) to (4-12), which is used to regenerate a damaged site of a peripheral nerve and/or central nerve.

(4-14) The nerve regeneration-inducing material according to any one of (4-1) to (4-10), which is used to regenerate a damaged site of a nerve branch and/or nerve plexus.

(4-15) The nerve regeneration-inducing material according to (4-14), wherein the damaged site of a nerve branch and/or nerve plexus is present in at least one location selected from the group consisting of the prostate gland, arm, brain, spinal cord, face, neck, waist (lumbar region), sacrum, lumbosacrum, genitals, heart, abdominal cavity and within the intestinal wall.

(4-15a) The nerve regeneration-inducing material according to (4-14), wherein the damaged site of a nerve branch and/or nerve plexus is present in at least one location selected from the group consisting of the prostate gland, bladder, cavernous body, arm, extremities, brain, spinal cord, face, neck, waist (lumbar region), sacrum, lumbosacrum, genitals, heart, abdominal cavity, lower abdomen, pelvis, within the thoracic cavity and within the intestinal wall.

(4-16) The nerve regeneration-inducing material according to (4-13), which is used to regenerate nerve damage accompanying lymph node dissection.

(4-17) A method for inducing regeneration of a damaged site of a nerve in a subject in need of regeneration of a damaged site of a nerve, the method including a step for applying the nerve regeneration-inducing material according to any one of (4-1) to (4-14) to a damaged site of a nerve.

(4-17a) The low endotoxin bioabsorbable polysaccharide having a carboxyl group in a molecule thereof for use in regenerating a damaged site of a nerve, which uses the nerve regeneration-inducing material according to any one of (4-1) to (4-14).

(4-17c) A use of the low endotoxin bioabsorbable polysaccharide having a carboxyl group in a molecule thereof and/or at least one type of crosslinking reagent selected from a compound represented by the above-mentioned general formula (I) and a salt thereof to produce the nerve regeneration-inducing material according to any one of (4-1) to (4-14), wherein the nerve regeneration-inducing material is used so as to regenerate a nerve by applying to a damaged site of a nerve.

In addition, the present invention provides a nerve regeneration-inducing material as indicated below as a fifth aspect thereof.

(5-1) A non-tubular nerve regeneration-inducing material used to regenerate a damaged site of a nerve, containing: (A) a crosslinked form obtained by covalent bond crosslinking a low endotoxin bioabsorbable polysaccharide having a carboxyl group in a molecule thereof with at least one type of crosslinking reagent selected from a compound represented by the following general formula (I) and a salt thereof, and (B) a bioabsorbable polymer:

(wherein $R^1$ and $R^2$ respectively and independently represent a hydrogen atom or group represented by the formula: —COCH($NH_2$)—($CH_2$)$_4$—$NH_2$, and n represents an integer of 2 to 18).

(5-2) The nerve regeneration-inducing material according to (5-1), wherein the bioabsorbable polysaccharide having a carboxyl group in a molecule thereof is at least one type selected from the group consisting of alginic acid, an ester thereof and a salt thereof.

(5-3) The nerve regeneration-inducing material according to either of (5-1) or (5-2), wherein the crosslinking reagent is an N-hydroxysuccinimide salt of a compound represented by the above-mentioned general formula (I).

(5-4) The nerve regeneration-inducing material according to (5-3), wherein the N-hydroxysuccinimide salt of a compound represented by the above-mentioned general formula (I) is at least one type selected from the group consisting of a 2N-hydroxysuccinimide salt of diaminoethane, a 2N-hydroxysuccinimide salt of diaminohexane, a 4N-hydroxysuccinimide salt of N,N'-di(lysyl)-diaminoethane and a 3N-hydroxysuccinimide salt of N-(lysyl)-diaminohexane.

(5-5) The nerve regeneration-inducing material according to any one of (5-1) to (5-4), which is in the form of a xerogel.

(5-6) The nerve regeneration-inducing material according to any one of (5-1) to (5-5), wherein the bioabsorbable polymer is at least one type selected from the group consisting of polyglycolic acid, polylactic acid and a copolymer thereof, and polycaprolactone.

(5-7) The nerve regeneration-inducing material according to any one of (5-1) to (5-6), which is irradiated with an electron beam and/or gamma rays at an adsorbed dose of 1 kGy to 100 kGy.

(5-8) The nerve regeneration-inducing material according to any one of (5-1) to (5-7), wherein, after cutting the material to a size measuring 2 cm long×2 cm wide (without specifying thickness), clamping the material at a location 5 mm away from one of cut surfaces with a double clip so as to interpose the same (clamped portion A) and immersing a region up to 10 mm from a cut surface (B) opposing the clamped portion A of the material in physiological saline for 15 minutes, and then a tensile tear test is carried out at a speed of 10 mm/min with the clamped portion A horizontal to a square surface of the material by passing a needle, with a suture through the center of a location 5 mm away from the cut surface (B) of the material and immobilizing both ends of the suture with a clamp, the maximum test force (load) is 0.10 (N) to 10.0 (N).

(5-9) The nerve regeneration-inducing material according to any one of (5-2) to (5-8), wherein the content of at least one type selected from the group consisting of alginic acid, an ester thereof and a salt thereof in the material is 0.2 mg/cm² to 12 mg/cm² as sodium alginate.

(5-10) The nerve regeneration-inducing material according to any one of (5-1) to (5-9), wherein the content of bioabsorbable polymer in the material is 0.05 mg/cm² to 30 mg/cm².

(5-11) The nerve regeneration-inducing material according to any one of (5-1) to (5-10), which is used to regenerate a damaged site of a peripheral nerve and/or central nerve.

(5-12) The nerve regeneration-inducing material according to any one of (5-1) to (5-11), which is used to regenerate a damaged site of a nerve branch and/or nerve plexus.

(5-13) The nerve regeneration-inducing material according to (5-12), wherein the damaged site of a nerve branch and/or nerve plexus is present in at least one location selected from the group consisting of the prostate gland, bladder, cavernous body, arm, extremities, brain, spinal cord, face, neck, waist (lumbar region), sacrum, lumbosacrum, genitals, heart, abdominal cavity, lower abdomen, pelvis, within the thoracic cavity and within the intestinal wall.

(5-14) The nerve regeneration-inducing material according to any one of claims (5-1) to (5-13), which is used for at least one type of regeneration of nerve damage selected from the group consisting of regeneration of nerve damage accompanying tumor resection, lymph node dissection and/or trauma, and regeneration of nerve damage accompanying tissue reconstruction.

(5-15) The nerve regeneration-inducing material according to any one of (5-2) to (5-14), wherein the weight average molecular weight (absolute molecular weight) as measured by GPC-MALS of at least one type selected from the group consisting of the low endotoxin alginic acid, ester thereof and salt thereof is 80,000 or more.

(5-16) The nerve regeneration-inducing material according to any one of (5-2) to (5-15), wherein the M/G ratio of at least one type selected from the group consisting of the low endotoxin alginic acid, ester thereof and salt thereof is 0.4 to 3.0.

(5-17) A method for inducing regeneration of nerve damage, the method including a step for applying the nerve regeneration-inducing material according to any one of (5-1) to (5-16) to a damaged site of a nerve of a subject in need of treatment.

(5-18) The low endotoxin bioabsorbable polysaccharide having a carboxyl group in a molecule thereof for use in regeneration of a damaged site of a nerve, including applying the nerve regeneration-inducing material according to any one of (5-1) to (5-16) to a damaged site of a nerve of a subject in need of treatment.

(5-18a) A use of the low endotoxin bioabsorbable polysaccharide having a carboxyl group in a molecule thereof and/or at least one type of crosslinking reagent selected from a compound represented by the above-mentioned general formula (I) and a salt thereof to produce the nerve regeneration-inducing material according to any one of (5-1) to (5-16), wherein the nerve regeneration-inducing material is used so as to regenerate a nerve by applying to a damaged site of a nerve.

(5-19) A method for adjusting the residual time in the body of a nerve regeneration-inducing material, the method at least including the following step: irradiating (A) a crosslinked form obtained by covalent bond crosslinking a low endotoxin bioabsorbable polysaccharide having a carboxyl group in a molecule thereof with at least one type of crosslinking reagent selected from a compound represented by the above-mentioned general formula (I) and a salt thereof; and (B) a crosslinked form containing a bioabsorbable polymer, with an electron beam and/or gamma rays.

In addition, the present invention provides a method for producing a nerve regeneration-inducing material as indicated below as a sixth aspect thereof.

(6-1) A method for producing a nerve regeneration-inducing material at least including the steps of:

(1) mixing a solution containing a low endotoxin bioabsorbable polysaccharide having a carboxyl group in a molecule thereof and at least one type of crosslinking reagent selected from a compound represented by the above-mentioned general formula (I) and a salt thereof;

(2) placing in a mold the mixture obtained in (1) with a bioabsorbable polymer and allowing the same to stand undisturbed for a certain amount of time to obtain a crosslinked form;

(3) washing the crosslinked form obtained in (2) followed by lyophilization; and (4) irradiating the crosslinked form obtained in (3) with an electron beam and/or gamma rays.

In addition, the present invention provides a nerve regeneration-inducing material as indicated below as a seventh aspect thereof.

(7-1) A non-tubular nerve regeneration-inducing material containing a crosslinked form obtained by covalent bond crosslinking a low endotoxin bioabsorbable polysaccharide having a carboxyl group in a molecule thereof with at least one type of crosslinking reagent selected from a compound represented by the following general formula (I) and a salt thereof:

$$R^1HN-(CH_2)_n-NHR^2 \quad (I)$$

(wherein $R^1$ and $R^2$ respectively and independently represent a hydrogen atom or group represented by the formula: $-COCH(NH_2)-(CH_2)_4-NH_2$, and n represents an integer of 2 to 18); wherein, when four pieces of the material cut to a size of 1 cm long×1 cm wide (without specifying thickness) and 25 mL of physiological saline are placed in a 50 mL volume centrifuge tube and a biodegradation test is carried out by shaking at a reciprocating shaking rate of 120 times/min at a temperature of 50° C. in a constant-temperature shaking water bath, the residual rate of the sample 72 hours after starting shaking is 10% to 80%.

(7-2) The nerve regeneration-inducing material according to (7-1), wherein the residual rate 72 hours after the start of shaking in the above-mentioned biodegradation test demonstrates a decrease in comparison with the residual rate 4 hours after the start of shaking.

(7-3) The nerve regeneration-inducing material according to either of (7-1) or (7-2), wherein the residual rate 4 hours after the start of shaking in the above-mentioned biodegradation test is 55% or more.

(7-4) The nerve regeneration-inducing material according to any one of (7-1) to (7-3), wherein the bioabsorbable polysaccharide having a carboxyl group in a molecule thereof is at least one type selected from the group consisting of alginic acid, an ester thereof and a salt thereof.

(7-5) The nerve regeneration-inducing material according to any one of (7-1) to (7-4), wherein the crosslinking reagent is an N-hydroxysuccinimide salt of a compound represented by the above-mentioned general formula (I).

(7-6) The nerve regeneration-inducing material according to (7-5), wherein the N-hydroxysuccinimide salt of a compound represented by the above-mentioned general formula (I) is at least one type selected from the group consisting of a 2N-hydroxysuccinimide salt of diaminoethane, a 2N-hydroxysuccinimide salt of diaminohexane, a 4N-hydroxysuccinimide salt of N,N'-di(lysyl)-diaminoethane and a 3N-hydroxysuccinimide salt of N-(lysyl)-diaminohexane.

(7-7) The nerve regeneration-inducing material according to any one of (7-1) to (7-6), which is in the form of a xerogel.

(7-8) The nerve regeneration-inducing material according to any one of (7-1) to (7-7), which is irradiated with an electron beam and/or gamma rays at an adsorbed dose of 1 kGy to 100 kGy.

(7-9) The nerve regeneration-inducing material according to any one of (7-1) to (7-8), further containing a bioabsorbable polymer.

(7-10) The nerve regeneration-inducing material according to (7-9), wherein the bioabsorbable polymer is at least one type selected from the group consisting of polyglycolic acid, polylactic acid and a copolymer thereof, and polycaprolactone.

(7-11) The nerve regeneration-inducing material according to any one of (7-1) to (7-10), wherein, after cutting the material to a size measuring 2 cm long×2 cm wide (without specifying thickness), clamping the material at a location 5 mm away from one of cut surfaces with a double clip so as to interpose the same (clamped portion A) and immersing a region up to 10 mm from a cut surface (B) opposing the clamped portion A of the material in physiological saline for 15 minutes, and then a tensile tear test is carried out at a speed of 10 mm/min with the clamped portion A horizontal to a square surface of the material by passing a needle with a suture through the center of a location 5 mm away from the cut surface (B) of the material and immobilizing both ends of the suture with a clamp, the maximum test force (load) is 0.10 (N) to 10.0 (N).

(7-12) The nerve regeneration-inducing material according to any one of (7-4) to (7-11), wherein the content of at least one type selected from the group consisting of alginic acid, an ester thereof and a salt thereof in the material is 0.2 mg/cm$^2$ to 12 mg/cm$^2$ as sodium alginate.

(7-13) The nerve regeneration-inducing material according to any one of (7-1) to (7-12), wherein the content of bioabsorbable polymer in the material is 0.05 mg/cm$^2$ to 30 mg/cm$^2$.

(7-14) The nerve regeneration-inducing material according to any one of (7-1) to (7-13), which is used to regenerate a damaged site of a peripheral nerve and/or central nerve.

(7-15) The nerve regeneration-inducing material according to any one of (7-1) to (7-14), which is used to regenerate a damaged site of a nerve branch and/or nerve plexus.

(7-16) The nerve regeneration-inducing material according to (7-15), wherein the damaged site of a nerve branch and/or nerve plexus is present in at least one location selected from the group consisting of the prostate gland, bladder, cavernous body, arm, extremities, brain, spinal cord, face, neck, waist, sacrum, lumbosacrum, genitals, heart, abdominal cavity, lower abdomen, pelvis, within the thoracic cavity and within the intestinal wall.

(7-17) The nerve regeneration-inducing material according to any one of (7-1) to (7-16), which is used for at least one type of regeneration of nerve damage selected from the group consisting of regeneration of nerve damage accompanying tumor resection, lymph node dissection and/or trauma, and regeneration of nerve damage accompanying tissue reconstruction.

(7-18) The nerve regeneration-inducing material according to any one of (7-4) to (7-17), wherein the weight average molecular weight (absolute molecular weight) as measured by GPC-MALS of at least one type selected from the group consisting of the low endotoxin alginic acid, ester thereof and salt thereof is 80,000 or more.

(7-19) The nerve regeneration-inducing material according to any one of (7-4) to (7-18), wherein the M/G ratio of at least one type selected from the group consisting of the low endotoxin alginic acid, ester thereof and salt thereof is 0.4 to 3.0.

(7-20) A method for inducing regeneration of nerve damage, the method including a step for applying the nerve regeneration-inducing material according to any one of (7-1) to (7-19) to nerve damage of a subject in need of treatment.

(7-21) The low endotoxin bioabsorbable polysaccharide having a carboxyl group in a molecule thereof for use in a method for inducing regeneration of a damaged site of a nerve, the method including applying the nerve regeneration-inducing material according to any one of (7-1) to (7-19) to nerve damage of a subject in need of treatment.

(7-21a) A use of the low endotoxin bioabsorbable polysaccharide having a carboxyl group in a molecule thereof and/or at least one type of crosslinking reagent selected from a compound represented by the above-mentioned general formula (I) and a salt thereof to produce the nerve regeneration-inducing material according to any one of (7-1) to (7-19), wherein the nerve regeneration-inducing material is used so as to regenerate a nerve by applying to a damaged site of a nerve.

(7-22) A method for adjusting the residual time in the body of a nerve regeneration-inducing material, the method at least including the following step: irradiating a material, containing a crosslinked form obtained by covalent bond crosslinking a low endotoxin bioabsorbable polysaccharide having a carboxyl group in a molecule thereof with at least one type of crosslinking reagent selected from a compound represented by the above-mentioned general formula (I) and a salt thereof, with an electron beam and/or gamma rays.

Effect of Invention

The nerve regeneration-inducing material of the present invention may provide a novel treatment means that makes it possible to promote regeneration of a damaged site of a nerve branch and/or nerve plexus for which there is currently no useful treatment method other than autologous nerve graft.

In addition, in one aspect of the present invention, the amount of time the nerve regeneration-inducing material is eliminated in the body is controlled, thereby resulting in a superior nerve regeneration inducing effect.

The nerve regeneration-inducing material of the present invention can be applied and induce nerve regeneration in the case in which the damaged site of a nerve is linear, in the case in which the damaged site of a nerve is a nerve branch and/or nerve plexus, or in the case in which the stump of a nerve defect cannot be visualized, thereby having a wide range of clinical application.

In several aspects of the present invention, the nerve regeneration-inducing material is in the form of a xerogel and/or sheet, and is able to enfold a nerve stump or junction so as to cover with the nerve regeneration-inducing material due to the abundant flexibility thereof. As a result of being in the form of a xerogel and/or sheet, the nerve regeneration-inducing material can be used by cutting to a size suitable for the affected area where used at the time of use, thereby eliminating the need to prepare in advance multiple sizes corresponding to the inner diameter of a nerve. In addition, the material of the present invention can also be applied to a damaged site of a nerve endoscopically or laparoscopically and the like.

In one of several aspects of the present invention, a nerve regeneration-inducing material further containing a bioabsorbable polymer is provided with suitable strength and can be used by suturing when applying to an affected area with suture. On the other hand, the material of the present invention can also be used without suturing, and in the case of not suturing, offers the advantage of enabling medical treatment to be carried out comparatively easily.

The nerve regeneration-inducing material of the present invention has superior safety and biocompatibility since it is eliminated from the body after a certain amount of time has elapsed.

In one aspect of the present invention, the nerve regeneration-inducing material further containing a bioabsorbable polymer has suitable strength, is difficult to be torn even if it is placed around the knee or other locations of movement, and is able to stably regenerate nerve damage. In addition, the material of the present invention offers the advantages of having a shape that is resistant to deformation in the production process, demonstrating superior handling and having high production efficiency.

The material for nerve regeneration of the present invention fulfills any one or more of the above-mentioned effects.

MODES FOR CARRYING OUT INVENTION

Figure 1:
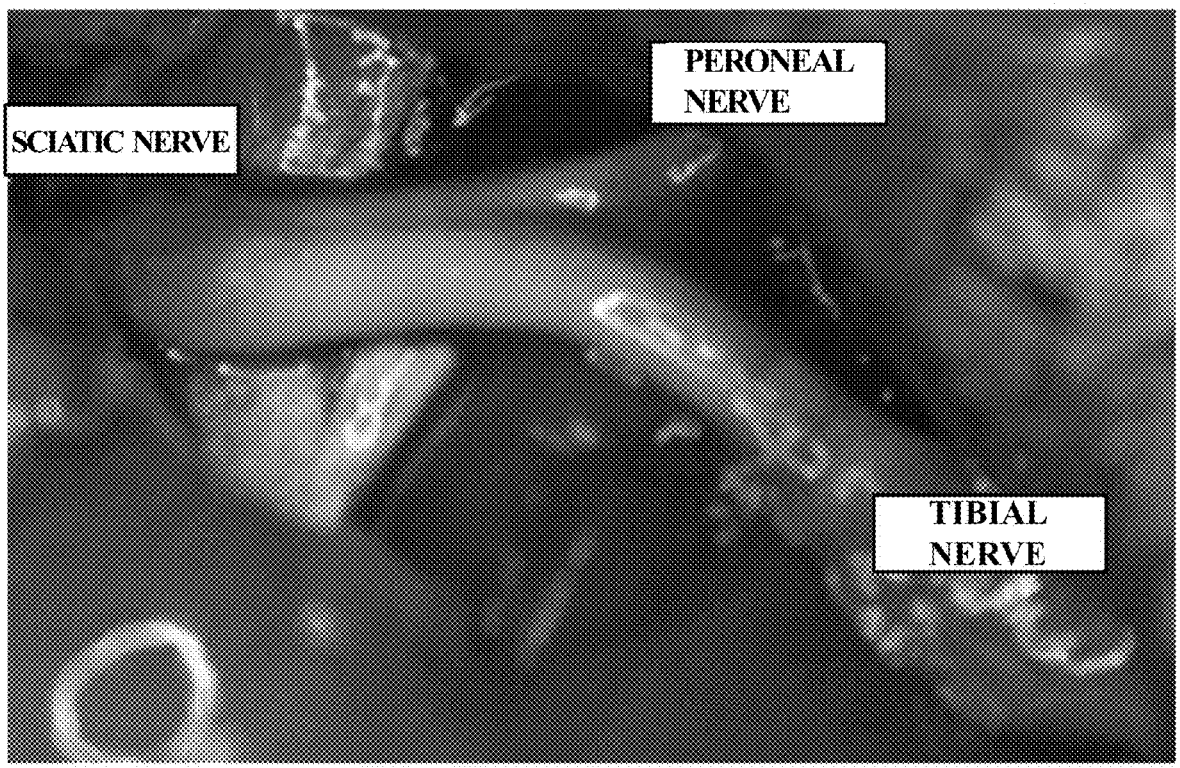
FIG. 1 is a photograph taken 8 weeks after having applied A-3EDA.PGA50 to a defective branch of sciatic nerve.

1. Bioabsorbable Polysaccharide Having Carboxyl Group in Molecule Thereof

In one of the several aspects of the present invention, a nerve regeneration-inducing material can be produced using one or two or more types of a bioabsorbable polysaccharide having a carboxyl group in a molecule thereof. Examples of bioabsorbable polysaccharides having a carboxyl group in a molecule thereof include polysaccharides such as alginic acid, carboxymethyl starch, hyaluronic acid and carboxymethyl cellulose, esters thereof and salts thereof. The bioabsorbable polysaccharide is preferably degraded and absorbed in the body. In addition, the polysaccharide is preferably a bioabsorbable polysaccharide free of cell adhesion. The polysaccharide is preferably at least one type selected from alginic acid, an ester thereof and a salt thereof. Furthermore, in the present description, the "nerve regeneration-inducing material" may also be referred to as the "material of the present invention".

2. Alginic Acid, Ester Thereof and Salt Thereof

The "alginic acid", "alginic acid ester" and "alginic acid salt" used in the present invention may be a naturally-occurring or synthetic and is preferably naturally-occurring. In the present description, "at least one type selected from alginic acid, an ester thereof and a salt thereof" may also be simply referred to as "alginic acid". The alginic acid preferably used in the present invention is a bioabsorbable polysaccharide extracted from brown algae such as Lessonia, Macrocystis, Laminaria, Ascophyllum, Durvillea, Cottidae, Eisenia or kelp that is a polymer obtained by linearly polymerizing two types of uronic acid in the form of D-mannuronic acid (M) and L-guluronic acid (G). More specifically, the alginic acid is a block copolymer obtained by arbitrarily bonding a homopolymer fraction of D-mannuronic acid (MM fraction), a homopolymer fraction of L-guluronic acid (GG fraction) and a fraction in which D-mannuronic acid and L-guluronic acid are randomly arranged (M/G fraction).

The composite ratio of D-mannuronic acid to L-guluronic acid in the alginic acid (M/G ratio) varies mainly according to the type of algae or other biological organism serving as the source thereof and is also affected by the habitat of that biological organism and season, and the M/G ratio extends over a wide range from a high G type in which the M/G ratio is about 0.2 to a high M type in which the M/G ratio is about 5. The gelling ability of the alginic acid is such that the properties of the formed gel are affected by the M/G ratio, and in general, a higher ratio of G is known to result in higher gel strength. M/G ratio also has an effect on such properties as gel hardness, brittleness, water absorption and flexibility. The M/G ratio of the alginic acid and/or salt thereof used in the present invention is normally 0.2 to 4.0, more preferably 0.4 to 3.0 and even more preferably 0.5 to 3.0. In the present invention, a numerical range indicated using the word "to" indicates a range that includes those values indicated before and after the word "to" as the minimum value and maximum value, respectively, thereof.

Although there are no particular limitations thereon, the "alginic acid ester" and "alginic acid salt" used in the present invention are required not to have a functional group that does not inhibit the crosslinking reaction in order to allow the crosslinking agent to react. Examples of alginic acid esters preferably include propylene glycol alginate.

Examples of alginic acid salts include monovalent salts of alginic acid and divalent salts of alginic acid.

Examples of monovalent salts of alginic acid preferably include sodium alginate, potassium alginate and ammonium alginate, more preferably sodium alginate or potassium alginate, and particularly preferably sodium alginate.

Examples of divalent salts of alginic acid preferably include calcium alginate, magnesium alginate, barium alginate and strontium alginate.

Alginic acid is a high molecular weight polysaccharide, and although it is difficult to accurately determine the molecular weight thereof, the weight average molecular weight thereof is typically within the range of 1,000 to 10,000,000, preferably within the range of 10,000 to 8,000,000, and more preferably within the range of 20,000 to 3,000,000. When measuring the molecular weight of naturally-occurring high molecular weight substances, differences are known to occur in the resulting values depending on the measurement method.

For example, weight average molecular weight as measured by gel permeation chromatography (GPC) or gel filtration chromatography (and these may also be collectively referred to as size exclusion chromatography) is preferably 100,000 or more, more preferably 500,000 or more, and preferably 5,000,000 or less and more preferably 3,000,000 or less. The range thereof is preferably 100,000 to 5,000,000 and more preferably 500,000 to 3,500,000.

In addition, absolute weight average molecular weight, for example, can be measured by GPC-MALS. Weight average molecular weight as measured by GPC-MALS (absolute molecular weight) is preferably 10,000 or more, more preferably 80,000 or more, even more preferably 90,000 or more, and preferably 1,000,000 or less, more preferably 800,000 or less, even more preferably 700,000 or less and particularly preferably 500,000 or less. The range thereof is preferably 10,000 to 1,000,000, more preferably 80,000 to 800,000, even more preferably 90,000 to 700,000, and particularly preferably 90,000 to 500,000.

Normally, in the case of calculating the molecular weight of a high molecular weight polysaccharide using a method like that described above, measurement error occurs at the rate of about 10% to 20%. For example, molecular weight of 400,000 can have a range of fluctuation of 320,000 to 480,000, a molecular weight of 500,000 can have a range of fluctuation of 400,000 to 600,000, and a molecular weight of 1,000,000 can have a range of fluctuation of 800,000 to 1,200,000.

The molecular weight of alginic acid can be measured in accordance with an ordinary method.

Typical conditions in the case of using gel permeation chromatography to measure molecular weight are as described in Example 1 of the present description. Columns consisting of two of GMPW-XL columns and one G2500PW-XL column (7.8 mm I.D.×300 mm) can be used for the columns, eluent can be, for example, 200 mM aqueous sodium nitrate solution and pullulan can be used for the molecular weight standard.

Typical conditions in the case of using GPC-MALS to measure molecular weight are as described in Example 1 of the present description. An RI detector or multi-angle light scattering (MALS), for example, can be used for the detector.

Although there are no particular limitations thereon, viscosity of the alginic acid used in the present invention in the case of measuring as an 1 w/w % solution of alginic acid is preferably 10 mPa·s to 1,000 mPa·s and more preferably 50 mPa·s to 800 mPa·s.

Viscosity of an aqueous solution of alginic acid can be measured in accordance with ordinary methods. For example, viscosity can be measured according to the rotational viscometer method using a coaxial double cylinder rotational viscometer, single cylinder rotational viscometer (Brookfield viscometer) or cone and plate rotational viscometer (cone-plate rotational viscometer). Viscosity is preferably measured according to the viscosity measurement method of the Japanese Pharmacopoeia (16th edition). In the present invention, a cone-plate rotational viscometer is used more preferably. Typical measurement conditions in this case are as described in Example 1 of the present invention.

Although alginic acid initially has a large molecular weight and high viscosity after being extracted from brown algae, molecular weight and viscosity decrease during the course of heat-drying and purification. Alginic acid having different molecular weights can be produced by a technique such as management of temperature and other conditions of the production process, selection of the brown algae serving as raw material or fractionating molecular weight in the production process. Moreover, alginic acid having a target molecular weight can also be produced by mixing different lots of alginic acid having different molecular weights or viscosities.

The bioabsorbable polysaccharide having a carboxyl group in a molecule thereof used in the present invention is a low endotoxin bioabsorbable polysaccharide. Low endotoxin refers to a low endotoxin level to a degree that substantially does not cause inflammation or fever. More preferably, a bioabsorbable polysaccharide subjected to endotoxin reduction treatment is desirable.

Endotoxin reduction treatment can be carried out according to a known method or method complying therewith. For example, endotoxin reduction treatment can be carried out by, for example, the method of Suga, et al. involving purification of sodium hyaluronate (see, for example, Japanese Patent Application Publication No. H09-324001), the method of Yoshida, et al. involving purification of β1,3-glucan (see, for example, Japanese Patent Application Publication No. H08-269102), the method of William, et al. involving purification of a biopolymer salt such as alginate or gellan gum (see, for example, Japanese Translation of PCT Application Publication No. 2002-530440), the method of James, et al. involving the purification of polysaccharide (see, for example, WO 1993/13136), the method of Lewis, et al. (see, for example, U.S. Pat. No. 5,589,591), the method of Herrman Frank, et al. involving the purification of alginate (see, for example, Appl. Microbiol. Biotechnol. (1994) 40: 638-643) or methods complying therewith. The endotoxin reduction treatment of the present invention is not limited thereto, but rather can be carried out by a known method, or a suitable combination thereof, such as washing, filtration using a filter (such as endotoxin removal filter or charged filter), ultrafiltration, purification using a column (such as an endotoxin affinity adsorption column, gel filtration column or column using an ion exchange resin), adsorption to a hydrophobic substance, resin or activated charcoal, organic solvent treatment (such as extraction with an organic solvent or precipitation or sedimentation by adding an organic solvent) or surfactant treatment (see, for example, Japanese Patent Application Publication No. 2005-036036). A known method such as centrifugal separation may be suitably combined with these treatment steps. Endotoxin reduction treatment is preferably selected according to the type of alginic acid.

Endotoxin level can be confirmed by a known method. For example, endotoxin level can be measured by a method using a limulus reagent (LAL) or a method using the Endospecy (registered trademark) ES-24S Set (Seikagaku Corporation).

Although there are no particular limitations on the method used to treat endotoxins in the bioabsorbable polysaccharide used in the present invention, the endotoxin content of the bioabsorbable polysaccharide as a result thereof as measured with a limulus reagent (LAL) is preferably 500 endotoxin units (EU)/g or less, more preferably 100 endotoxin units (EU)/g or less, still more preferably 50 EU/g or less, and particularly preferably 30 EU/g or less. Sodium alginate subjected to endotoxin reduction treatment can be acquired in the form of commercial products such as Sea Matrix (registered trademark) (Mochida Pharmaceutical Co., Ltd.) or PRONOVA™ UP LVG (FMC BioPolymer).

3. Crosslinking Reagent

The crosslinking reagent preferably used in the present invention is at least one type selected from an amine-based compound included in a compound represented by the following general formula (I) and a salt thereof. In the present description, a compound represented by the following general formula (I) may be referred to as amine-based compound (I):

$$R^1HN-(CH_2)_n-NHR^2 \quad (I)$$

(wherein $R^1$ and $R^2$ respectively and independently represent a hydrogen atom or group represented by the formula: —COCH(NH$_2$)—(CH$_2$)$_4$—NH$_2$, and n represents an integer of 2 to 18).

Specific examples thereof include diaminoalkanes and/or salts thereof such as diaminoethane, diaminopropane, diaminobutane, diaminopentane, diaminohexane, diaminoheptane, diaminooctane, diaminononane, diaminodecane, diaminododecane or diaminooctadecane, and mono- or di(lysyl)diaminoalkanes and/or salts thereof such as N-(lysyl)-diaminoethane, N,N'-di(lysyl)-diaminoethane, N-(lysyl)-diaminohexane or N,N'-di(lysyl)-diaminohexane, and one or two or more types of these diamines and salts thereof can be used.

Among these, compounds and/or salts thereof in which n in the above-mentioned general formula (I) is 2 to 8 are used preferably for the amine-based compound (I) and/or salt thereof. In the case the crosslinking reagent is composed of a salt of the amine-based compound (I), N-hydroxysuccinimide is preferably used as the component that forms a salt.

A 2N-hydroxysuccinimide salt of diaminoethane, a 2N-hydroxysuccinimide salt of diaminohexane, a 4N-hydroxysuccinimide salt of N,N'-di(lysyl)-diaminoethane or a 3N-hydroxysuccinimide salt of N-(lysyl)-diaminohexane is particularly preferably used for the crosslinking reagent composed of amine-based compound (I) and/or salt thereof since safety and biocompatibility are even higher, and nerve regenerative action of an acid crosslinked form, obtained by covalent bond crosslinking with the crosslinking reagent, is more favorable.

4. Production of Nerve Regeneration-Inducing Material

Although the following provides an explanation of the production of the nerve regeneration-inducing material containing crosslinked alginate using alginic acid as an example of a bioabsorbable polysaccharide having a carboxyl group in a molecule thereof, the nerve regeneration-inducing material can be produced in compliance with that described below with respect to other polysaccharides as well.

The xerogel-like crosslinked alginate of the present invention can be obtained by, for example, mixing and dissolving an aqueous solution of alginic acid, the above-mentioned crosslinking reagent and a dehydration condensing agent such as water-soluble carbodiimide, pouring into a mold to gel and washing the gel followed by lyophilizing the same.

Although the crosslinking reaction can normally be carried out at a temperature of 4° C. to 37° C., it is preferably carried out over a range of 20° C. to 30° C. from the viewpoint of reaction efficiency.

In the case the nerve regeneration-inducing material contains another component other than the crosslinked alginate, there are no particular limitations on the order of the step for containing other another component, and for example, the step for containing another component may be before or after lyophilization.

In one aspect of the present invention, the nerve regeneration-inducing material of the present invention is preferably in the form of a xerogel. A xerogel refers to a state in which a gel has been dried. Although gels contain a solvent such as water in a three-dimensional network structure, a xerogel consists only of the network after having lost the solvent. In the present description, a xerogel may also be referred to as a "sponge".

A solution of alginic acid can be prepared according to a known method or a method complying therewith. Although there are no particular limitations on the solvent provided it is a solvent that can be applied to the body, the solvent is preferably an aqueous solvent, and preferable examples thereof include purified water, distilled water, ion exchange water, Milli-Q water, physiological saline, phosphate-buffered saline and DMSO. These are preferably sterilized and subjected to endotoxin reduction treatment.

Crosslinking rate can be controlled by the molar ratio of the crosslinking reagent used and the duration of the crosslinking reaction. Lowering the crosslinking rate allows the obtaining of a flexible crosslinked form having a high moisture content, while increasing the crosslinking rate results in greater rigidity and lower moisture content. Crosslinking rate is suitably selected according to the application of the crosslinked form.

Although there are no particular limitations thereon, the molar ratio of the crosslinking reagent used is preferably within the range of 1 mol % to 50 mol %, and more preferably within the range of 5 mol % to 40 mol %, based on the total number of carboxyl groups possessed by the alginic acid.

With respect to the duration of the crosslinking reaction, since the crosslinking reaction proceeds with time, the reaction time can be prolonged in the case a high crosslinking rate is required. Reaction time is normally within the range of 6 hours to 96 hours and preferably within the range of 24 hours to 72 hours from the viewpoint of reaction efficiency.

In addition, the crosslinking reaction does not allow the obtaining of a crosslinked form having adequate mechanical strength if the solution concentration of alginic acid is excessively low, while if the concentration of alginic acid is excessively high, excessive time is required to dissolve the alginic acid and the moisture content of the resulting crosslinked form is low resulting in a hard crosslinked form, thereby making this undesirable. Thus, the solution concentration of alginic acid is preferably within the range of 0.1% to 5% and more preferably within the range of 0.5% to 3%.

Although the crosslinked form obtained according to the crosslinking reaction per se demonstrates practical strength and stability, it may be used in combination with other gelation methods such as ionic bond crosslinking or hydrophobic bond crosslinking according to the application.

In several aspects of the present invention, in the case the nerve regeneration-inducing material of the present invention contains at least one type (of alginic acid) selected from the group consisting of alginic acid, ester thereof and salt thereof, the content of alginic acid per 1 cm$^2$ of the material is preferably 0.2 mg/cm$^2$ to 12 mg/cm$^2$, more preferably 0.5 mg/cm$^2$ to 7 mg/cm$^2$, even more preferably 1 mg/cm$^2$ to 6 mg/cm$^2$, and particularly preferably 1 mg/cm$^2$ to 5 mg/cm$^2$ as sodium alginate. In the present description, the term "alginic acid content" represents the value obtained by converting the amount of alginic acid contained in the material to the amount of sodium alginate.

In a preferable aspect of the present invention, the nerve regeneration-inducing material of the present invention may contain one or two or more types of bioabsorbable polymer such as polyglycolic acid, polylactic acid, a copolymer thereof or polycaprolactone in addition to the bioabsorbable polysaccharide having a carboxyl group in a molecule thereof. A known example of a copolymer of polyglycolic acid and polylactic acid (also referred to as "PLGA" in the in the present description) is polyglactin. These polymers are used as suture materials and the like, have bioabsorbability and demonstrate superior biocompatibility. Although there are no particular limitations on the form of these bioabsorbable polymers, a nonwoven fabric, woven fabric, mesh or needle punch and the like can be used preferably, while that in the form of a nonwoven fabric, mesh or needle punch is used more preferably. For example, a bioabsorbable polymer in the form of a nonwoven fabric sheet may be spread out on a tray, and a solution obtained by dissolving a bioabsorbable polysaccharide and crosslinking agent and the like may be filled into the tray and allowed to gel. There are no particular limitations on the arrangement of the bioabsorbable polysaccharide having a carboxyl group in a molecule thereof and the bioabsorbable polymer in the nerve regeneration-inducing material of the present invention. A layer of the bioabsorbable polysaccharide having a carboxyl group in a molecule thereof and a layer of the bioabsorbable polymer may be laminated, a layer of the bioabsorbable polysaccharide having a carboxyl group in a molecule thereof may be interposed between two layers of the bioabsorbable polymer, or a mixture of both may be present in a single layer. In Example 5-(4) of the present description, since the crosslinked alginate of the present invention demonstrates an action that induces nerve regeneration irrespective of the PGA content thereof, materials other than PGA can be used in the same manner instead of PGA. These bioabsorbable polymers are able to enhance strength of the crosslinked form and improve handling of the nerve regeneration-inducing material. In Example 7 of the present description, since a crosslinked form produced using a PLGA content roughly equal to that of a crosslinked form produced using PGA indicates similar degradability, these bioabsorbable polymers were suggested to be able to be used in the same manner in the present invention. In one aspect of the present invention, the bioabsorbable polymer used in the nerve regeneration-inducing material of the present invention is a polymer that contains polyglycolic acid, and preferably polyglycolic acid and/or a copolymer of polyglycolic acid and polylactic acid (PLGA).

In one preferable aspect of the present invention, the nerve regeneration-inducing material of the present invention may preferably contain 0.05 mg/cm$^2$ to 30 mg/cm$^2$, more preferably 0.1 mg/cm$^2$ to 10 mg/cm$^2$, even more preferably 0.5 mg/cm$^2$ to 7 mg/cm$^2$, and particularly preferably 1 mg/cm$^2$ to 5 mg/cm$^2$ of the bioabsorbable polymer. As a result of the nerve regeneration-inducing material of the present invention containing these bioabsorbable polymers, the nerve regeneration-inducing material of the present invention is provided with strength that enables it to be sutured, is able to prevent deformation attributable to lyophilization, and is able to enhance production efficiency. In addition, in the examples of the present invention, since a nerve regeneration-inducing material containing these bioabsorbable polymers is observed to tend to have fewer examples of inadequate regeneration of nerve damage in comparison with material not containing a bioabsorbable polymer, strength of a crosslinked form was suggested to be able to enhanced, the crosslinked form is resistant to rupture even in the knee or other locations of movement, and is able to stably regenerate axons as a result of containing the bioabsorbable polymer.

In one of several aspects of the present invention, the nerve regeneration-inducing material may also contain other polysaccharides or polymers within a range that does not impair the effect of the nerve regeneration-inducing material of the present invention. Among these, since heparin has been confirmed to have an effect such as controlled release of heparin-binding growth factors, the nerve regeneration-inducing material of the present invention can also contain heparin. Furthermore, in several aspects of the present invention, the nerve regeneration-inducing material does not contain heparin.

In addition, in one of the several aspects of the present invention, the nerve regeneration-inducing material may also contain a factor useful for nerve growth. Examples of factors useful for nerve growth include, but are not limited to, basic fibroblast growth factor (bFGF) and nerve growth factor (NGF). However, the nerve regeneration-inducing material of the resent invention is able to demonstrate the effect of inducing nerve regeneration even in the case of not containing a factor useful for nerve growth. In several aspects of the present invention, the nerve regeneration-inducing material does not contain these factors.

A material containing crosslinked alginate obtained by a crosslinking reaction can normally be purified by removing unreacted reagent and dehydration condensing agent with a washing solution. Although there are no particular limitations thereon, water or extracellular fluid (ECF) and the like can be used for the washing solution. ECF can be produced by dissolving CaCl$_2$ (2.5 mM) or NaCl (143 mM) in purified water. ECF may also be used after having passed through a sterilizing filter as necessary. After having washed the material containing the crosslinked alginate with ECF, the crosslinked alginate is preferably washed with water to remove residual calcium. The nerve regeneration-inducing material of the present invention may be used in the form of a gel prior to lyophilization.

Lyophilization of the crosslinked alginate can be carried out using common general technical knowledge known among persons skilled in the art. Lyophilizing conditions can be suitably adjusted and a primary drying step and secondary drying step and the like may be provided.

In one of the several aspect of the present invention, although there are no particular limitations thereon, the form of the nerve regeneration-inducing material of the present invention can be suitably selected in consideration of, for example, the range of the damaged site of a nerve where the material is to be applied. For example, when in the form of a xerogel, although the material can adopt a non-tubular shape (such as in the shape of a sheet, curve, or sheet with surface irregularities) and tubular shape, it is preferably non-tubular and more preferably in the form of a sheet. When the nerve regeneration-inducing material is in the form of a sheet, since the nerve regeneration-inducing material can be applied to a damaged site by further cutting to match the range of the damaged site of a nerve, there are no particular limitations on the size of the sheet. For example, when the shape of the sheet is represented as the length×width×height (thickness), there are no particular limitations on the lengths of the length and width, and the height (thickness) is preferably 0.2 mm to 30 mm, more preferably 0.3 mm to 15 mm, even more preferably 0.5 mm to 10 mm, and particularly preferably 1 mm to 10 mm. More preferably, in addition to the height (thickness) being as indicated above, the lengths of the length and width are 1 mm to 300 mm×1 mm to 300 mm, respectively, particularly preferably 3 mm to 200 mm×3 mm to 200 mm, respectively, and even more preferably 5 mm to 150 mm×5 mm to 150 mm, respectively. Furthermore, thickness is not required to be uniform, but rather a gradient structure may be employed in which one side is thick while the other side is thin.

In one of the several aspects of the present invention, the nerve regeneration-inducing material is preferably subjected to sterilization treatment. Examples of sterilization include, but are not limited to, gamma ray sterilization, electron beam sterilization, ethylene oxide gas sterilization and ethanol sterilization. In several aspects of the present invention, sterilization effects can be obtained as a result of irradiating the crosslinked form with an electron beam or gamma rays and the like.

5. Nerve Regeneration-Inducing Material Irradiated with Electron Beam and/or Gamma Rays In several aspects of the present invention, a nerve regeneration-inducing material is provided that contains a crosslinked form, obtained by covalent bond crosslinking a low endotoxin bioabsorbable polysaccharide having a carboxyl group in a molecule thereof with the above-mentioned amine-based compound (I) and/or a salt thereof, which is irradiated with an electron beam and/or gamma rays. In this aspect, the target of the electron beam and/or gamma ray radiation may be only the crosslinked form in which the bioabsorbable polysaccharide is covalently bonded with the above-mentioned crosslinking agent, or may be a crosslinked form containing other components in the case the nerve regeneration-inducing material contains other components such as a bioabsorbable polymer or nerve growth factor. In addition, other components can also be contained in the crosslinked form after having irradiated with an electron beam and/or gamma rays.

An electron beam is one type of particle beam that has an electrical charge in the radiation and is used for the purpose of sterilization and the like. An electron beam can be radiated using an electron accelerator and the like. Since an electron beam is able to pass through materials, it can be used to sterilize complex shapes and occluded areas, and is characterized by absence of concern over residual substances following treatment. The dose of an electron beam is related to such factors as voltage, current and irradiation time (transport speed of the irradiated object). Since an electron beam has less penetrating power than gamma rays, it is possible to the control the required penetrating power. Dose rate (dose per unit time) is 5,000 to 10,000 times higher than gamma rays, enabling treatment to be performed in a short period of time (several seconds to one minute).

Gamma rays are a type of electromagnetic waves present in radiation and are used for the purpose of sterilization and the like. Gamma rays can be radiated using a radiation source exposure device. Gamma rays have strong penetrability and the dose of gamma rays is related to such factors as heat source intensity, distance from heat source and irradiation time, and deterioration of the irradiated object is comparatively large due to treatment time requiring several hours.

In the present invention, although either an electron beam or gamma rays can be used, an electron beam is used more preferably from the viewpoints of ease of controlling the radiation dose to a constant level, ease of irradiating the irradiated object at a uniform dose and waste treatment of cobalt 60 of the gamma ray radiation source.

In one of the several aspects of the present invention, the nerve regeneration-inducing material of the present invention is irradiated with an electron beam and/or gamma rays at an absorbed dose of preferably 1 kGy to 100 kGy, more preferably 3 kGy to 60 kGy, even more preferably 5 kGy to 40 kGy, particularly preferably 5 kGy to 25 kGy, and still more preferably 10 kGy to 24 kGy.

The nerve regeneration-inducing material irradiated with an electron beam and/or gamma rays of several aspects of the present invention has a shorter amount of time until it is eliminated from the site where applied in the body in comparison with non-irradiated materials, or in other words, is characterized by having a short residual time in the body. "Elimination from the site where applied" refers to the crosslinked form no longer being able to be visualized during observation with the naked eye when the crosslinked form has been placed at the applied site and the applied site has been observed after a certain period of time. Although the site where applied in the body at this time is preferably a damaged site of a nerve, elimination from the applied site may be confirmed by carrying out a subcutaneous or intramuscular implantation test using a rat or other animal.

A nerve regeneration-inducing material irradiated with an electron beam and/or gamma rays in this manner is characterized by having a high effect of inducing nerve regeneration in comparison with non-irradiated materials.

In several aspects of the present invention, the nerve regeneration-inducing material of the present invention is eliminated from the applied site preferably in 7 days to 270 days, more preferably 14 days to 180 days, even more preferably 14 days to 150 days, and particularly preferably 14 days to 120 days. In addition, in one aspect of the present invention, at least a portion of the nerve regeneration-inducing material of the present invention is preferably observed to remain when a subcutaneous implantation test has been carried out in a rat using the material having a size of 0.7 cm long×1.5 cm wide (without specifying thickness) and evaluating after 4 weeks since implantation by staining tissue at the implantation site in accordance with the description of Example 6 of the present description.

In another aspect of the present invention, when a degradation test is carried out on 4 pieces of the nerve regeneration-inducing material of the present invention by placing the material cut to a size of 1 cm long×1 cm wide (without specifying thickness) and 25 mL of physiological saline are placed in a centrifuge tube having a volume of 50 mL followed by shaking at a reciprocating shaking rate of 120 times/min at a temperature of 50° C. in a constant-temperature shaking water bath in accordance with the description of Example 7 of the present description, the residual rate of the material 72 hours after the start of shaking is preferably 10% to 80% and more preferably 20% to 80%. The "residual rate" referred to herein refers to the ratio of the mass weight of the material after having dried the material under reduced pressure at 60° C. to a constant weight after carrying out the degradation test for a certain amount of time to the mass weight of the material prior to the start of the degradation test. In addition, the length and width of the cut surface of the material are taken to be intersecting perpendicularly. Although the thickness of the material targeted for testing can be used as is for the thickness of the material at this time, a standard thickness is preferably about 1 mm to about 10 mm.

In addition, in one aspect of the present invention, the residual rate of the nerve regeneration-inducing material of the present invention 72 hours after the start of the above-mentioned degradation test preferably indicates a decrease in comparison with the residual rate 4 hours after the start of the degradation test. In the examples of the present invention, although the effect of inducting nerve regeneration of an ethanol-sterilized crosslinked alginate was determined to be inadequate, the residual rate of a crosslinked form of the same composition exceeded 100% even at 72 hours after the start of the degradation test in Example 7.

In addition, in one aspect of the present invention, the residual rate of the nerve regeneration-inducing material of the present invention 4 hours after the start of the above-mentioned degradation test is preferably 55% or more and more preferably 60% or more. In the examples of the present description, although the nerve regeneration effect of a crosslinked form irradiated with an electron beam at a high dose of 40 kGy or 60 kGy was determined to be inadequate, this was thought to be due to the material not fulfilling the role of a nerve scaffold as a result of the crosslinked form being eliminated soon after having been installed at a damaged site as indicated by the fact that the crosslinked form irradiated with a high-dose electron beam exhibited a decrease in the residual rate thereof immediately after (4 hours after) the start of the degradation test.

In one aspect of the present invention, the residual rate of the nerve regeneration-inducing material of the present invention 4 hours after the start of the above-mentioned degradation test is 55% or more, after which the residual rate thereof decreases, preferably demonstrating a residual rate of 10% to 80% 72 hours after the start of the degradation test.

In one aspect of the present invention, when the tear test described below (tear test described in Example 10) was carried out, the maximum test force of the nerve regeneration-inducing material of the present invention is preferably 0.10 (N) to 10.0 (N) and more preferably 0.10 (N) to 5.0 (N).

The tear test in the present invention is carried out in the following manner. The target material is cut to a size of 2 cm long×2 cm wide (without specifying thickness). The cut surfaces of the length and width are taken to intersect perpendicularly. Although the thickness of the material targeted for testing can be used as is for the thickness of the material at this time since the test is carried out for the purpose of determining tear strength of the material per se, a standard thickness is preferably about 1 mm to about 10 mm. The material is then clamped with a double clip at a location 5 mm away from one of the cut surfaces thereof (clamped portion A). The region up to 10 mm from a cut surface (B) opposing the clamped portion A of the material is immersed in physiological saline for 15 minutes. A needle with a suture is passed through the center of a location 5 mm away from the cut surface (B) of the material and both ends of the suture are immobilized with an instrument. With the clamped portion A horizontal to a square surface of the material, the material is pulled until tearing at a speed of 10 mm/min, and this tensile load is measured as test force (N). The point of maximum test force is taken to be the maximum test force (N). Although measurement of tensile load is preferably carried out using a compact physical property testing machine (EZ-Graph, Shimadzu Corporation), in the case such an instrument is unable to be acquired, a load measuring machine similar thereto may be used.

The size of the double clip used for the clamped portion A is preferably such that the width of the clamping portion is 15 mm to 19 mm. Although the suture used in the test is preferably Vicryl (registered trademark) having a thickness of "4-0", in the case this is unable to be acquired, suture may be used that is composed of polyglactin 910 (glycolic acid/lactate-based polyester: 90/10) for the material and has a thickness of 4-0. Although an SH-1 round needle is preferably used for the needle, in the case this is unable to be acquired, a suture-compatible needle similar thereto may be used.

In the case of determining the maximum test force of the material, preferably n=3 to 10 pieces of the material are cut and used to measured test force followed by determining the average value of that maximum test force which is then used as the maximum test force of the material.

The present invention also provides a method for adjusting the residual time in the body of the nerve regeneration-inducing material that at least includes a step for irradiating the nerve regeneration-inducing material containing a crosslinked form, obtained by covalent bond crosslinking a low endotoxin bioabsorbable polysaccharide having a carboxyl group in a molecule thereof with the above-mentioned amine-based compound (I) and/or a salt thereof with an electron beam and/or gamma rays. The present invention also provides a method for adjusting the residual time in the body of the nerve regeneration-inducing material that at least includes a step for irradiating a crosslinked form, containing (A) a crosslinked form obtained by covalent bond crosslinking a low endotoxin bioabsorbable polysaccharide having a carboxyl group in a molecule thereof with at least one type of crosslinking reagent selected from a compound represented by the above-mentioned general formula (I) and a salt thereof, and (B) a bioabsorbable polymer with an electron beam and/or gamma rays. The residual time in the body of the nerve regeneration-inducing material can be adjusted by increasing the radiation dose of an electron beam and/or gamma rays in order to shorten the residual time in the body of the material of the present invention, or conversely decreasing the radiation dose of an electron beam and/or gamma rays in order to prolong residual time in the body.

The present invention also provides a method for producing a nerve regeneration-inducing material that at least includes a step for irradiating a material containing a crosslinked form, obtained by covalent bond crosslinking using a low endotoxin bioabsorbable polysaccharide having a carboxyl group in a molecule thereof and the amine-based compound (I) and/or a salt thereof, with an electron beam and/or gamma rays. The "material containing a crosslinked form" may arbitrarily include other components such as the above-mentioned bioabsorbable polymer or factor useful for nerve growth in addition to the crosslinked form produced with the bioabsorbable polysaccharide having a carboxyl group in a molecule thereof. Specific preferable aspects thereof are as previously described.

The present invention also provides a method for producing the nerve regeneration-inducing material that at least includes the following steps:

(1) a step for mixing a solution containing a low endotoxin bioabsorbable polysaccharide having a carboxyl group in a molecule thereof and at least one type of crosslinking reagent selected from a compound represented by the above-mentioned general formula (I) and a salt thereof, (2) a step for placing in a mold the mixture obtained in (1) with a bioabsorbable polymer and allowing the same to stand undisturbed for a certain amount of time to obtain a crosslinked form, (3) a step for washing the crosslinked form obtained in (2) followed by lyophilizing the same, and (4) a step for irradiating the crosslinked form obtained in (3) with an electron beam and/or gamma rays.

Preferable aspects of this production method are as described in the present description.

6. Usage

In several aspects of the present invention, the nerve regeneration-inducing material induces nerve regeneration and/or reconstruction by applying to a damaged site of a nerve that has occurred due to trauma or tumor resection and the like. The nerve regeneration-inducing material of the present invention demonstrates superior safety since it is absorbed and degraded after the several months normally required for nerve reconstruction and ultimately metabolized and excreted from the body.

In the present invention, "nerve damage" includes a state in which the continuity of a nerve is lost (defect) and a state in which nerve function is impaired even though nerve continuity is maintained, as well as division of a nerve and the like. In the present description, a "defect" refers to the case of a "gap" or "severed site" and the like, and includes "neurotmesis".

Although nerve damage occurs caused by, for example, trauma, tumor resection, lymph node dissection or diseases of the central and peripheral nervous systems and the like, in the present invention, there are no limitations on the cause of the occurrence of nerve damage. For example, during neurorrhaphy or autologous nerve graft, since a state can form in which a gap forms between locations that are not sutured at those sites where a nerve is joined with another nerve, the nerve regeneration-inducing material can be applied to such sites. In addition, the nerve regeneration-inducing material can also be used to regenerated nerve damage occurring during, for example, reconstruction of tissue that has become deficient, lost or resected due to various factors.

In the present invention, "applying" refers to placing the nerve regeneration-inducing material at a damaged site of a nerve. In the case a damaged site of a nerve consists of a defect, although it is not necessary to contact the nerve regeneration-inducing material with the stump of the nerve, the material of the present invention is preferably placed so that the nerve regeneration-inducing material contacts the stump of the nerve, and more preferably, the material of the present invention is placed so that the nerve regeneration-inducing material and the nerve stump overlap. The nerve regeneration-inducing material does not have to necessarily contact the stump of a nerve in cases such as when the stump of the nerve cannot be visualized.

The material for inducing nerve generation may be applied such that, for example, the nerve regeneration-inducing material is placed so as to contact both ends of the nerve to be reconstructed from one direction, both ends of a nerve interpose the nerve regeneration-inducing material either above and below or to the left and right in the state of the surgical site, or the nerve regeneration-inducing material is placed so as to cover the entire periphery of both ends of a nerve.

When the nerve regeneration-inducing material is non-tubular, nutrients and oxygen required for nerve axon growth are easily supplied in comparison with tubular materials, while on the other hand, since this is also advantageous for nerve axon growth since entry of fibrous tissue acting on tissue repair is prevented, the material is preferably non-tubular and more preferably in the form of a sheet. In this case, fibrous tissue acting on tissue recovery impairs recovery of normal tissue due to scarring. In Example 8 of the present description, the crosslinked alginate of the present invention was found to be provided with preferable performance for use as a nerve regeneration-inducing material by demonstrating the effect of inhibiting adhesion and proliferation of fibroblasts in comparison with a collagen sponge.

In the present invention, "inducing nerve regeneration" refers to promoting the proliferation of nerve cells and/or elongation of nerve axons. In the case a damaged site of a nerve constitutes a defect, "inducing nerve regeneration" means that elongation of nerve axons is promoted so as to restore nerve continuity. When a defect occurs caused by damage or crushing of a nerve, since the continuity of nerve axons on the peripheral side from the defect (located distally from the stump) is interrupted from nerve cell bodies, degeneration (referred to as Waller degeneration in the case of peripheral nerves) occurs resulting in a loss of nerve function. Degenerated nerve axons located distal to a defect are phagocytized by macrophages and the like as remnants. Subsequently, a large number of nerve axons that have sprouted from the stump on the central side extend to a stump on the peripheral side. Axons that have extended from the central side preferably connect with a stump on the peripheral side. Alternatively, induction of nerve regeneration can also be indicted by at least a partial recovery of nerve function or sensation that had previously been lost. Induction of nerve regeneration in the present invention does not necessarily refer to complete recovery to the state prior to nerve damage. The nerve regeneration-inducing material of the present invention preferably achieves one or more of the above-mentioned effects.

Usage of the nerve regeneration-inducing material of the present invention comprises exposing a nerve site to be reconstructed in a subject, preparing the nerve regeneration-inducing material of a suitable size corresponding to the length and width of the nerve to be reconstructed, and then applying the material to a damaged site of the nerve to be reconstructed. The "subject" here refers to a human, an organism other than a human, such as a bird or non-human mammal (including, for example, a cow, monkey, cat, mouse, rat, guinea pig, hamster, pig, dog, rabbit, sheep and horse).

Although it is necessary to align the thickness of a tubular material to the thickness of a nerve at the applied site, this is not necessary in the case of a sheet, and the material can be applied by cutting to match the size of the damaged site.

When the nerve regeneration-inducing material is in the form of a xerogel, the material may be applied as is in a dry state or may be applied in the form of a gel after incorporating physiological saline or purified water and the like therein. Namely, the nerve regeneration-inducing material of the present invention may also be in the form of a gel.

Although it is not necessary to suture the nerve regeneration-inducing material to a damaged site of a nerve after having applied the nerve regeneration-inducing material to the damaged site of a nerve, the nerve regeneration-inducing material and the damaged site of a nerve (such as a nerve stump) may be sutured as necessary.

In several aspects of the present invention, the nerve regeneration-inducing material is applied to a damaged site of a nerve branch and/or nerve plexus. A nerve plexus refers to a nerve network, while a branched nerve refers to a site that forms a network structure. The nerve regeneration-inducing material of the present invention is preferably applied to a damaged site of a nerve branch and/or nerve plexus, and can be applied to, for example, the prostate gland, bladder, cavernous body, arm, extremities, brain, spinal cord, face, neck, waist (lumbar region), sacrum, lumbosacrum, genitals, heart, abdominal cavity, lower abdomen, pelvis, within the thoracic cavity and within the intestinal wall.

In several aspects of the present invention, there are no particular limitations on the site where the nerve regeneration-inducing material can be applied provided it is a damaged site of a nerve. The nerve regeneration-inducing material can be used to induce regeneration of a damaged site of a peripheral nerve and/or central nerve, and can be applied to a damaged site of a linear nerve or nerve branch and/or nerve plexus. Examples of central nerves include damaged sites of nerves of the brain and spinal cord.

In several aspects of the present invention, the nerve regeneration-inducing material of the present invention may be used in combination with factors useful for nerve regeneration or growth, humoral factors such as physiologically active substances, or cells. Although there are no particular limitations on the method of combined use, these factors or cells may be incorporated in the nerve regeneration-inducing material of the present invention, for example. There no particular limitations on humoral factors provided they are factors that can be supplementarily used for regenerated tissue, and examples thereof include bFGF, NGF, hepatocyte growth factor, immunosuppressants and anti-inflammatory agents. Examples of cells include, but are not limited to, mesenchymal stem cells, bone marrow mesenchymal stem cells, neural stem cells, bone marrow-derived mononuclear cells, adipose-derived stem cells, in vivo pluripotent stem cells, ES cells, neural progenitor cells, iPS cells and CD133-positive cells, obtained by autologous or heterologous culturing. In another aspect of the present invention, an aspect of the nerve regeneration-inducing material of the present invention not used in combination with these cells or factors is also preferable, and more preferably, the material is not used in combination with CD133-positive cells.

Although there no particular limitations thereon, methods for evaluating nerve regeneration, such as by evaluating elongation of nerve axons, are as described in Examples 4 and 5 of the present description, in which the elongation of nerve axons may be indicated by observing axon elongation at a target site by light microscopy or embedding a nerve in Epon resin followed by staining with a reagent such as toluidine blue, anti-beta tubulin class 3 antibody or anti-S 100 antibody and counting the number of myelinated axons between a gap for which have reached a stump on the peripheral side in accordance with ordinary methods. After having embedded using a suitable method such as by embedding in Epon resin, the state of regenerated axons can be evaluated by observing with a transmission electron microscope (TEM) or scanning electron microscope (SEM).

In addition, nerve regeneration may also be evaluated by, for example, electrophysiological measurement, histopathological evaluation, walking pattern, tracer detective study for investigating axoplasmic transport or two-point discrimination.

Compound muscle action potentials (CMAPs) using recovery of motor nerve function as an indicator or somatosensory potentials (SEPs) using recovery of sensory nerve function as an indicator (see, for example, Journal of Materials Science: Materials in Medicine 16 (2005) pp. 503-509) can be used for electrophysiological measurement.

The present invention also provides a method for inducing nerve regeneration in a subject in need of regeneration of a damaged site of a nerve that includes a step for applying the previously described nerve regeneration-inducing material to a damaged site of a nerve. The present invention also provides a method for inducing regeneration of a damaged site of a nerve branch and/or nerve plexus in a subject in need of regeneration of a damaged site of a nerve branch and/or nerve plexus that includes a step for applying the previously described nerve regeneration-inducing material to a damaged site of a nerve branch and/or nerve plexus. Specific methods are as previously described.

Moreover, the present invention provides a use of a low endotoxin bioabsorbable polysaccharide having a carboxyl group in a molecule thereof and/or at least one type of crosslinking reagent selected from a compound represented by the above-mentioned general formula (I) and a salt thereof in order to produce the previously described nerve regeneration-inducing material, which is used so as to apply the above-mentioned nerve regeneration-inducing material to a damaged site of a nerve, and preferably to a damaged site of a nerve branch and/or nerve plexus. Specific uses are as previously described.

The present invention further provides the above-mentioned low endotoxin bioabsorbable polysaccharide having a carboxyl group in a molecule thereof for use in regenerating a damaged site of a nerve, and preferably a damaged site of a nerve branch and/or nerve plexus, using a nerve regeneration-inducing material that contains a crosslinked form obtained by covalent bond crosslinking the low endotoxin bioabsorbable polysaccharide having a carboxyl group in a molecule thereof with a crosslinking reagent selected from a compound represented by the above-mentioned general formula (I) and a salt thereof.

Although the following provides a more detailed explanation of the present invention by indicating examples thereof, the present invention is not limited thereto.

EXAMPLES

Example 1 Production of Crosslinked Alginate and Evaluation of Properties

Crosslinked alginate in the form of a xerogel was produced using sodium alginate and (i) calcium chloride, (ii) mixture of calcium chloride and sodium chloride, or (iii) ethylenediamine, respectively, as a crosslinking agent followed by evaluating the properties thereof.

1-(1) Sodium Alginate

Six types of low endotoxin sodium alginate each having an endotoxin content of less than 50 EU/g (Sea Matrix (registered trademark), Mochida Pharmaceutical Co., Ltd.) were used for the sodium alginate.

The M/G ratios of the sodium alginate of samples A-1, A-2 and A-3 ranged from 0.4 to 1.8 and the M/G ratios of the sodium alginate of samples B-1, B-2 and B-3 ranged from 0.1 to 0.4.

Furthermore, the viscosities and weight average molecular weights of 1 w/w % aqueous solutions of each sodium alginate are shown in Table 1.

Viscosity of the sodium alginate was measured using a rotational viscometer (cone-plate rotational viscometer) in accordance with the viscosity measurement method of the Japanese Pharmacopeia (16th edition). Specific measurement conditions were as indicated below. Sample solutions were prepared using Milli-Q water. A cone-plate rotational viscometer (RheoStress RS600 Viscoelasticity Measurement System (Thermo Haake GmbH) Sensor: 35/1) was used for the measuring instrument. The rotating speed was set to 1 rpm when measuring a 1 w/w % sodium alginate solution. Values were read by measuring for 2 minutes and determining the average value for 1 to 2 minutes from the start of measurement. The average value of three measurements was taken to be the measured value. Values were measured at a temperature of 20° C.

The weight average molecular weight of each sodium alginate was measured using two types of measurement methods consisting of gel permeation chromatography (GPC) and GPC-MALS. Measurement conditions were as indicated below.

Pretreatment Method

After dissolving the sample by adding eluent, the filtrate obtained by filtering the solution with a 0.45 μm membrane filter was used for the measurement solution.

(1) Measurement by Gel Permeation Chromatography (GPC)

Measurement Conditions (Measurement of Relative Molecular Weight Distribution)
Column: TSKgel GMPW-XL×2+G2500PW-XL (7.8 mm I.D.×300 mm×3 columns)
Eluent: 200 mM aqueous sodium nitrate solution
Flow rate: 1.0 mL/min
Concentration: 0.05%
Detector: RI detector
Column temperature: 40° C.
Injection volume: 200 μL
Molecular weight standards: standard pullulan, glucose (2) Measurement of GPC-MALS Measurement of Refractive Index Increment (dn/dc) (Measurement Conditions)
Differential refractometer: Optilab T-rEX
Measurement wavelength: 658 nm
Measurement temperature: 40° C.
Solvent: 200 mM aqueous sodium nitrate solution
Sample concentration: 0.5 mg/mL to 2.5 mg/mL (5 concentrations)

Measurement Conditions (Measurement of Absolute Molecular Weight Distribution)
Column: TSKgel GMPW-XL×2+G2500PW-XL (7.8 mm I.D.×300 mm×3 columns)
Eluent: 200 mM aqueous sodium nitrate solution
Flow rate: 1.0 mL/min
Concentration: 0.05%
Detector: RI detector, multi-angle light scattering (MALS) detector
Column temperature: 40° C.
Injection volume: 200 μL

TABLE 1

|   |     | Viscosity of 1 w/w % solution (mPa · s) | Weight average molecular weight GPC | Weight average molecular weight GPC-MALS | M/G ratio |
|---|-----|-----------------------------------------|-------------------------------------|------------------------------------------|-----------|
| A | A-1 | 10 to 40                                | 300,000 to 400,000                  | 60,000 to 80,000                         | 0.4 to 1.8 |
|   | A-2 | 50 to 150                               | 700,000 to 1,000,000                | 100,000 to 200,000                       |           |
|   | A-3 | 300 to 600                              | 1,100,000 to 1,700,000              | 200,000 to 400,000                       |           |
| B | B-1 | 10 to 40                                | 400,000 to 500,000                  | 70,000 to 90,000                         | 0.1 to 0.4 |
|   | B-2 | 70 to 150                               | 800,000 to 1,000,000                | 100,000 to 200,000                       |           |
|   | B-3 | 400 to 600                              | 1,500,000 to 1,900,000              | 200,000 to 350,000                       |           |

1-(2) Production of Crosslinked Alginate Using Calcium Chloride as Crosslinking Agent The following procedure was carried out in a room temperature environment (20° C. to 30° C.) unless specifically indicated otherwise. Each low endotoxin lyophilized sodium alginate shown in Table 1 was dissolved in Milli-Q water to obtain 1 w/v % aqueous sodium alginate solutions. Anhydrous calcium chloride was dissolved in Milli-Q water to obtain a 50 mM aqueous calcium chloride solution. 1 mL of 50 mM aqueous calcium chloride solution was layered into a tube (Falcon 2054) containing 1 mL of aqueous sodium alginate solution and allowed to stand still overnight followed by washing the resulting gelation product three times with Milli-Q water and lyophilizing to obtain crosslinked alginate in the form of a xerogel.

1-(3) Production of Crosslinked Alginate Using Calcium Chloride and Sodium Chloride as Crosslinking Agents Each low endotoxin lyophilized sodium alginate shown in Table 1 was dissolved in Milli-Q water to obtain 1 w/v % aqueous sodium alginate solutions. Anhydrous calcium chloride and sodium chloride were dissolved in Milli-Q water to produce an aqueous solution containing 4 mM calcium ions and 300 mM sodium ions (calcium-sodium crosslinking agent solution). 1 mL of the calcium-sodium crosslinking agent solution was layered in a tube (Falcon 2054) containing 1 mL of aqueous sodium alginate solution and was allowed to stand still overnight, followed by washing of the resulting gelation product three times with Milli-Q water and lyophilizing the same to obtain crosslinked alginate in the form of a xerogel.

Separate from the above, crosslinking agent solutions were prepared having a calcium ion concentration in the calcium-sodium crosslinking agent solution of 10 mM, 20 mM or 50 mM and crosslinked alginate was obtained according to the same procedure using the sodium alginate of sample A-1 or A-2.

1-(4) Production of Crosslinked Alginate Using Ethylenediamine as Crosslinking Agent 23 g of N-hydroxysuccinimide were dissolved in 1,000 mL of methanol. 6.7 mL of ethylenediamine were dissolved in 100 mL of methanol followed by adding to the N-hydroxysuccinimide solution and mixing. The resulting crystals were filtered with a glass filter and dried to obtain about 27.0 g of ethylenediamine 2N-hydroxysuccinimide (EDA.2HOSu).

2.2 mg of EDA.2HOSu and 16 mg of 1-ethyl-3-(3-dimethylaminopropyl)-carbodiimide hydrochloride (EDC.HCl) were added to 1 mL of a 1 w/v % aqueous sodium alginate solution, obtained by dissolving each low endotoxin sodium alginate shown in Table 1 in Milli-Q water, followed by dissolving therein.

The mixture was allowed to stand still for 2 days at room temperature in a Falcon 2054 tube to obtain a gel. After washing the gel with extracellular fluid (ECF) three times/day for about 7 days and then washing three times with Milli-Q water, the gel was lyophilized to obtain crosslinked alginate in the form of a xerogel. ECF was prepared by dissolving $CaCl_2$ (2.5 mM) and NaCl (143 mM) in purified water followed by being passed through a sterilizing filter and endotoxin removal filter and used for the procedure.

1-(5) Evaluation of Crosslinked Alginate

The crosslinked alginate obtained in the above-mentioned Examples 1-(2) through 1-(4) were evaluated from the viewpoints of gelation, porosity and residual in phosphate buffer saline (PBS).

Gelation was evaluated with a score of 3 in the case all of the solution gelled when observed visually after turning the tube upside-down, a score of 2 in the case roughly half the solution gelled, and a score of 1 in the case hardly any of the solution gelled.

Porosity was evaluated by measuring a cross-section of the crosslinked alginate at a magnification of 100× (acceleration voltage: 15 kV) using a scanning electron microscope after coating with gold, and assigning a score of 3 in the case of having uniform pores measuring 100 μm to 500 μm, assigning a score of 2 in the case of having irregularly sized pores, and assigning a score of 1 in the case of not having any pores.

The gel residual test in PBS was carried out by placing each gel in the shape of a square measuring about 5 mm on a side in 5 mL of PBS, observing the state of the gel after 1 week at 37° C., and assigning a score of 3 in the case nearly all the gel remained, assigning a score of 2 in the case roughly half the gel remained, and assigning a score of 1 in the case nearly all of the gel dissolved.

As a result, although some of the crosslinked form (i), obtained by using calcium chloride for the crosslinking agent, and the crosslinked form (ii), obtained by using calcium chloride and sodium chloride as crosslinking agents, were evaluated with a score of 3 for gelation, nearly all of the crosslinked forms scored 2 or 1 in evaluation of porosity and evaluation of the residual of the gel in PBS.

The results of evaluating the crosslinked alginate (iii), obtained by using ethylenediamine for the crosslinking agent, are shown in Table 2.

In the evaluation of gelation, although samples A-2, A-3, B-2 and B-3 gelled, gelation was inadequate in the case of samples A-1 and B-1.

In the evaluation of porosity, samples A-1, A-2 and A-3 were determined to allow the obtaining of porous bodies having pore sizes of 300 μm to 500 μm. On the other hand, pores were not observed in samples B-1, B-2 and B-3 and were in the form of fragments.

Evaluation of the residual of gel in PBS was such that, in contrast to roughly one-half of sample A-1 remaining after one week, transparent, aqueous gels remained after one week for nearly all of samples A-2, A-3, B-1, B-2 and B-3.

According to the above results, the sodium alginates of samples A-1, A-2 and A-3 (M/G ratio: 0.6 to 1.8) were determined to be used preferably in comparison with the sodium alginates of samples B-1, B-2 and B-3 (M/G ratio: 0.1 to 0.4) from the viewpoint of porosity.

In addition, among the sodium alginates of samples A-1, A-2 and A-3, the sodium alginates of samples A-2 and A-3, namely those sodium alginates having a weight average molecular weight as determined by GPS-MALS of 90,000 or more, were determined to be used preferably from the viewpoints of gelation and residual of the gel in PBS.

TABLE 2

Evaluation of crosslinked alginates by ethylenediamine

| | Evaluation Results | | |
|---|---|---|---|
| | Gelation | Porosity | Residual in PBS |
| A-1 | 1 | 3 | 2 |
| A-2 | 3 | 2 | 3 |
| A-3 | 3 | 3 | 3 |
| B-1 | 2 | 2 | 3 |
| B-2 | 3 | 1 | 3 |
| B-3 | 3 | 1 | 3 |

Example 2 Evaluation of Nerve-Like Cell Survival Rates

The crosslinked alginate produced in Example 1 (approx. 1.0 cm×1.0 cm) was impregnated with 1 mL of PC12 cells (50,000 cells/mL). After adding nerve growth factor (NGF) (final concentration: 100 ng/mL) and culturing for 7 days (while adding 0.5 mL of medium on day 3), WST-8 reagent (Dojindo laboratories) was added at 150 μL/well followed by allowing to stand undisturbed for 3 hours at 37° C. 100 μL aliquots of the supernatant were dispensed into a 96-well plate followed by measuring absorbance at 450 nm using a plate reader (Tecan Group Ltd.).

Four types of crosslinked alginate were prepared consisting of two types of sample A-2 obtained by respectively crosslinking with (i) calcium chloride and (iii) ethylenediamine (respectively referred to as A-2Ca and A-2EDA), and two types of sample A-3 obtained by respectively crosslinking with (i) calcium chloride and (iii) ethylenediamine (respectively referred to as A-3Ca and A-3EDA). A tissue culturing plate was used as a control.

As a result, the survival rates of A-2EDA, A-3Ca and A-3EDA were all 98% or higher based on a value of 100% for the survival rate of nerve-like cells of the control. On the other hand, survival rate was low for A-2Ca only (63%).

The reason for the low survival rate of the nerve like-cells for A-2Ca was presumed to toxicity attributable to eluted calcium and a shortage of the supply of oxygen due to an increased in viscosity of the medium caused by dissolved alginate.

Example 3 Evaluation of Crosslinked Alginate Irradiated with Electron Beam 3-(1) Irradiation of Crosslinked Alginate with Electron Beam Crosslinked alginates were prepared using low endotoxin sodium alginate samples A-2 and A-3 and using calcium chloride and sodium chloride as crosslinking agents (respectively referred to as A-2CaNa and A-3CaNa), or using ethylenediamine as crosslinking agent in accordance with Example 1-(4) (respectively referred to as A-2EDA and A-3EDA). The crosslinked alginates that used calcium chloride and sodium chloride as crosslinking agents were prepared by immersing plates filled with 3.15 mL aliquots of 1% aqueous sodium alginate solution in 25 mL of aqueous calcium-sodium crosslinking agent solution (calcium chloride anhydrate: 50 mM, sodium chloride: 300 mM) to induce gelation followed by washing and lyophilizing.

Each of the crosslinked alginates were irradiated with an electron beam at 20 kGy, 40 kGy and 60 kGy, respectively.

The Dynamitron-type electron accelerator manufactured by RDI was used for the electron irradiation device and the Shimadzu UV1800 spectrophotometer was used for measuring CTA dose. A CTA dosimeter (FTR-125, Fujifilm Corporation, Lot No.: 459) was used as a dosimeter. The electron beam was irradiated while adjusting irradiation time so as to yield the target radiation dose under conditions of an acceleration voltage of 4.8 MV and current of 20.0 mA.

3-(2) Evaluation of Disintegration Time of Electron Beam-Irradiated Crosslinked Alginate The electron beam-irradiated crosslinked alginates produced in Example 3-(1) and crosslinked alginate not irradiated with an electron beam were measured for disintegration time in physiological saline.

More specifically, each crosslinked form was cut to a size of about 7 mm×about 7 mm and placed in a 50 mL centrifuge tube filled with 25 mL of physiological saline followed by shaking at 60 rpm in an incubator at 37° C. with the centrifuge tube lying on its side and measuring the amount of time until the crosslinked form completely disintegrated.

The results are shown in Table 3.

The crosslinked alginates obtained by using calcium chloride and sodium chloride as crosslinking agents (A-2CaNa, A-3CaNa) were not observed to demonstrate a constant relationship between electron beam dose and time until dissolution. On the other hand, in the case of the crosslinked alginates obtained by using ethylenediamine as crosslinking agent (A-2EDA, A-3EDA), the amount of time until completion of dissolution became shorter as electron beam dose increased. Although both of the crosslinked forms of sample A-3EDA obtained at electron beam doses of 0 kGy and 20 kGy did not dissolve even after 20 days, in contrast to the non-irradiated crosslinked form maintaining its form even after 20 days, the crosslinked form following irradiation at 20 kGy did not maintain its sponge-like form and it was unable to be grabbed with tweezers due to its less hardness. In addition, sample A-2EDA was observed to tend to have a shorter amount of time until completion of dissolution overall in comparison with sample A-3EDA.

TABLE 3

| | Electron beam dose (kGy) | Time until completion of dissolution |
|---|---|---|
| A-2CaNa | 0 | 60 min |
| | 20 | 70 min |
| | 40 | 90 min |
| | 60 | 40 min |
| A-3CaNa | 0 | 6 days |
| | 20 | 90 min |
| | 40 | 70 min |
| | 60 | 60 min |
| A-2EDA | 0 | Not dissolved during 20 days of testing |
| | 20 | 1 day |
| | 40 | 220 min |
| | 60 | 80 min |
| A-3EDA | 0 | Not dissolved during 20 days of testing |
| | 20 | Not dissolved during 20 days of testing |
| | 40 | 1 day |
| | 60 | 320 min |

Example 4 Induction of Regeneration of Damaged Rat Sciatic Nerve Using Crosslinked Alginate Crosslinked alginate obtained by crosslinking with ethylenediamine was placed at the severed site of rat sciatic nerve (peripheral nerve) followed by evaluating the effect of inducing nerve regeneration.

4-(1) Production of Ethylenediamine-Crosslinked Alginates

Crosslinked alginates in the form of xerogels were obtained by covalent bond crosslinking the low endotoxin sodium alginates of samples A-2 and A-3 with ethylenediamine in accordance with Example 1-(4) (respectively referred to as A-2EDA and A-3EDA). The content of alginate in the crosslinked forms at this time was 3.0 mg/cm$^2$. The thickness of the crosslinked forms was about 2 mm to about 8 mm.

4-(2) Severing of Linear Sciatic Nerve and Induction of Regeneration by Ethylenediamine-Crosslinked Alginates The A-2EDA and A-3EDA prepared in the above-mentioned Example 4-(1) were used in the following experiment after sterilizing with ethanol.

The coating around the unbranched linear sciatic nerve of 4-week-old, male Wistar rats was decapsulated under anesthesia to expose the nerve. The nerve was bound with thread by placing a thread on the back side of the nerve, raising the nerve upward and placing a single crosslinked alginate sheet in the space beneath the nerve. The portion of the nerve located above the crosslinked alginate was severed to prepare a gap having a width of 7 mm to 8 mm. Subsequently, another crosslinked alginate sheet was placed over the severed site of the nerve so that the severed site of the nerve was interposed between two crosslinked alginate sheets. The two crosslinked alginate sheets were used at a size so as to be able to cover both nerve stumps on the central side and peripheral side. The crosslinked alginates were not immobilized by suturing. The opened muscle was sutured along with skin.

4-(3) Retrieval of Crosslinked Alginate and Evaluation of Regenerated Nerve Axons The crosslinked alginate and nerve were taken out from the surgical site in week 8 following the procedure performed in the above-mentioned Example 4-(2), and the peripheral nerve was removed from the crosslinked form. The removed nerve was primarily fixed in PBS containing 2.5% glutaraldehyde followed by secondarily fixing in PBS containing 2.0% osmium tetroxide. Following dehydration and replacement, the nerve was embedded in Epon resin. The embedded nerve was thinly sliced into sections having a thickness of 1 μm followed by staining with 0.5% toluidine blue. The stained sections were then observed with a light microscope and the number of myelinated axons was counted.

As a result, an average of 493 myelinated axons were confirmed for A-2EDA and an average of 524 myelinated axons were confirmed for A-3EDA in the peripheral side nerve in week 8, thereby confirming the effect of the crosslinked alginate on inducing nerve regeneration. However, those portions of the crosslinked alginate and nerve retrieved in week 8, the crosslinked alginate remaining hardly absorbed, were in the form of an enlarged tissue mass.

An average of 156 myelinated axons were confirmed in a group in which only the nerve was severed without installing crosslinked alginate provided as a comparative example. In addition, the average number of myelinated axons in an intact control group that did not undergo nerve severing was 8,918.

4-(4) Severing of Branched Site of Sciatic Nerve and Induction of Regeneration by Ethylenediamine-Crosslinked Alginate The A-2EDA prepared in the above-mentioned Example 4-(1) was used in the following experiment.

A nerve site where the common peroneal nerve and tibial nerve branch from the sciatic nerve in the shape of a Y was confirmed in 4-week-old, male Wistar rats under anesthesia followed by decapsulating the surrounding coating to expose the nerves. The sciatic nerve was bound with thread and raised up followed by placing a single crosslinked alginate sheet in the space beneath the nerve. The sciatic nerve, common peroneal nerve and tibial nerve were severed so as to form a gap of 7 mm to 8 mm, including the nerve branch. Subsequently, another crosslinked alginate sheet was placed above the severed site of the nerve so that the severed site of the nerve was interposed between two crosslinked alginate sheets. The two crosslinked alginate sheets were used at a size so as to be able to cover the nerve stumps on the central side and peripheral side. The crosslinked alginates were not immobilized by suturing. The opened muscle was sutured along with skin.

4-(5) Retrieval of Crosslinked Alginate and Evaluation of Regenerated Nerve Axons The crosslinked alginate and nerve were recovered from the surgical site in week 4 following the procedure performed in Example 4-(4), and the nerve located on the peripheral side of the crosslinked alginate was removed from the crosslinked form. Staining was carried out by using anti-beta tubulin class 3 antibody as antibody to axons and anti-S 100 antibody (Abcam plc.) as antibody to Schwann cells.

As a result, regeneration of axons was observed in both the stump on the side of the tibia and in the stump on the side of the fibula. Axon regeneration was observed in the gel surface layer at the site where the crosslinked form was implanted.

Example 5 Induction of Regeneration of Damaged Site of Rat Sciatic Nerve Using Electron Beam-Irradiated Crosslinked Alginate Containing Polyglycolic Acid 5-(1) Production of Electron Beam-Irradiated Ethylenediamine-Crosslinked Alginate Containing Polyglycolic Acid EDA.2HOSu and EDC.HCl were dissolved in the low endotoxin sodium alginate aqueous solution of sample A-2 in accordance with Example 1-(4). The resulting solution was filled into a tray in which was spread a nonwoven fabric sheet of polyglycolic acid (PGA) (100 mg/cc, 3.0 mg/cm$^2$, Non-woven PGA Biofelt, Biomedical Structures (USA)) followed by lyophilizing to produce a crosslinked alginate containing PGA designated as A-2EDA.PGA100. The content of alginate in the crosslinked form at this time was 2.0 mg/cm$^2$. More specifically, after having filled alginate solution into the tray having PGA spread therein and allowed gelation to sufficiently progress, the gel was washed to remove any unreacted crosslinking agent and reaction byproducts. A washing solution, obtained by passing extracellular fluid (ECF) (obtained by dissolving CaCl$_2$ (2.5 mM such as 0.28 g/L) and NaCl (143 mM, such as 8.36 g/L) in purified water) through a 0.22 μm filter (e.g., Millipak 20, Millipore Corporation) and endotoxin removal filter (Prep/Scale UF Cartridge PLGC CDUF 001 LG, Millipore Corporation), was used for the washing solution. The washing solution was suitably replaced followed by washing with distilled water and lyophilization after having removed any excess salt. The thickness of the resulting crosslinked form was about 2 mm to about 8 mm.

Similarly, a crosslinked alginate produced using the low endotoxin sodium alginate of sample A-3 was designated as A-3EDA.PGA100.

The resulting two types of crosslinked forms were irradiated with an electron beam at an absorbed dose of 20 kGy.

5-(2) Effect of Inducing Regeneration in Linear Sciatic Nerve

The two types of crosslinked forms obtained in Example 5-(1) (A-2EDA.PGA100 and A-3EDA.PGA100) were applied to gap of a linear sciatic nerve in accordance with Examples 4-(2) and 4-(3) followed by evaluation of the effect of inducing regeneration in the gap of the linear sciatic nerve 8 weeks after applying the crosslinked forms.

As a result, regeneration of myelinated nerve was observed extending from the gap towards the stump on the peripheral side in each group. The number of regenerated myelinated nerves was an average of 12,001 in the case of A-2EDA.PGA100 and an average of 7,010 in the case of A-3EDA.PGA100. In the present description, the number of regenerated myelinated nerves is determined by counting all myelinated nerves in a nerve bundle that is deemed to be the regenerated site present in a harvested tissue specimen. Since the number of axons in a healthy rat is roughly about 6,700, a sufficient number of regenerated myelinated nerves were determined to have been obtained.

5-(3) Regeneration Induction Effect on Sciatic Nerve Branch Defect

Two types of crosslinked alginates containing PGA were prepared using low endotoxin sodium alginate (sample A-2 or A-3) and a nonwoven polyglycolic acid (PGA) sheet (50 mg/cc, 1.5 mg/cm$^2$) in accordance with Example 5-(1) and were respectively designated as A-2EDA.PGA50 and A-3EDA.PGA50. The content of alginate in the crosslinked forms was 2.0 mg/cm$^2$. The thickness of the resulting crosslinked forms was about 2 mm to about 8 mm. The resulting two types of crosslinked forms were irradiated with an electron beam at an absorbed dose of 20 kGy. A total of four types of crosslinked alginates containing PGA, including the two types of crosslinked forms obtained in Example 5-(1) (A-2EDA.PGA100 and A-3EDA.PGA100), were subjected to the procedure in accordance with Example 4-(4) to evaluate the regeneration inducing effect on the gap of a branch of the sciatic nerve 8 weeks after application of the crosslinked forms.

Figure 2:
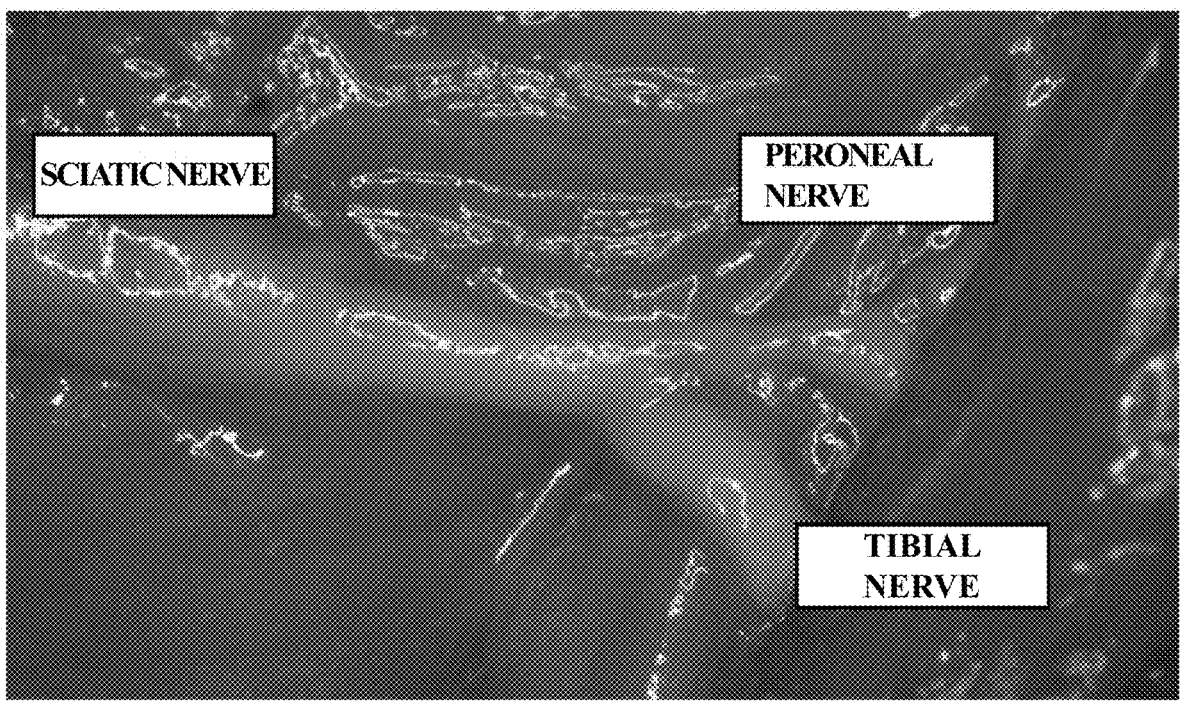
FIG. 2 is a photograph taken 8 weeks after having applied A-2EDA.PGA100 to a defective branch of sciatic nerve.

When external observations were made after 8 weeks, neural tissue was confirmed to be connected from the sciatic nerve to the tibial nerve and peroneal nerve in each group. As examples thereof, photographs taken after 8 weeks of procedures with respect to A-3EDA.PGA50 and A-2EDA.PGA100 are shown in FIGS. 1 and 2, respectively.

Figure 3:
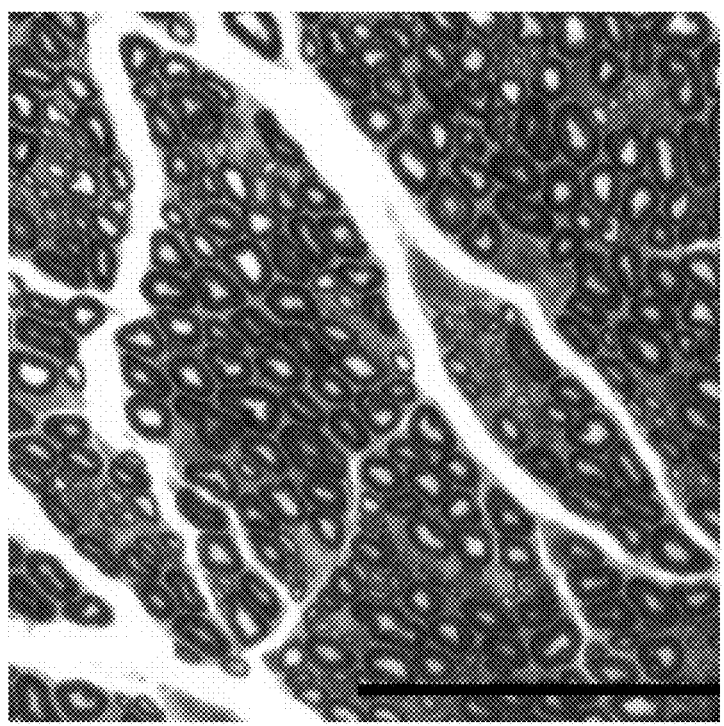
FIG. 3 is a photograph of stained regenerated axons on the side of the tibial nerve taken 8 weeks after having applied A-2EDA.PGA100 to a defective branch of sciatic nerve.
Figure 4:
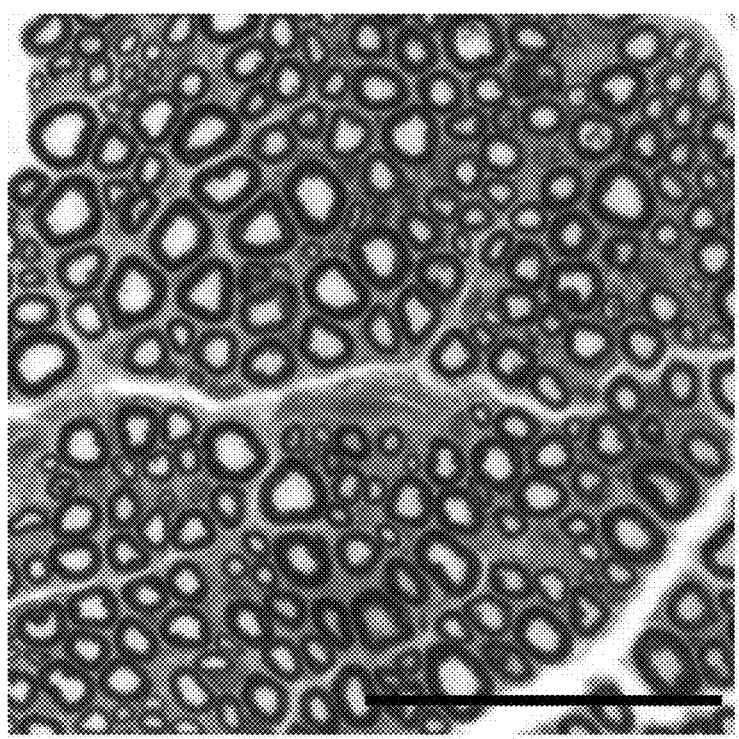
FIG. 4 is a photograph of stained regenerated axons on the side of the peroneal nerve taken 8 weeks after having applied A-2EDA.PGA100 to a defective branch of sciatic nerve.

In addition, the results of staining horizontal cross-sections of nerve at sites distal to the stump on the peripheral side using toluidine blue in accordance with Example 4-(3) are shown in FIGS. 3 and 4. FIG. 3 indicates a photograph of regenerated axons on the side of the tibial nerve, while FIG. 4 indicates a photograph of regenerated axons on the side of the peroneal nerve. As a result, the diameter of myelinated axons was longer, the number thereof was greater, the myelin was thicker and adequate regeneration was observed both on the side of the tibial nerve and on the side of the peroneal nerve. Namely, the nerve regeneration-inducing material of the present invention was shown to induce regeneration of both branching nerves in the case of using at a defective site of a nerve branch.

5-(4) Regeneration Induction Effect on Linear or Branched Sciatic Nerve Defect (2)

The effect of inducing regeneration on a gap in a branched site of rat sciatic nerve was evaluated for each of the following samples 8 weeks after applying a crosslinked form in accordance with Example 4.

An ethylenediamine-crosslinked alginate (alginate content: 2.0 mg/cm$^2$) was produced using the low endotoxin sodium alginate of sample A-2 in accordance with Example 1-(4) followed by irradiating with an electron beam at 20 kGy to obtain Sample No. 1.

The results obtained in Example 5-(3) are shown by designating the samples A-2EDA.PDA50 and A-2EDA.PDA100 used in Example 5-(3) as Sample Nos. 2 and 3, respectively.

A crosslinked form was produced using the low endotoxin sodium alginate of sample A-3 and PGA100 in accordance with Example 5-(1) (A-3EDA.PGA100). A crosslinked form having an alginic acid content of 2.0 mg/cm$^2$ was designated as Sample No. 4, a crosslinked form having an alginic acid content of 4.0 mg/cm$^2$ was designated as Sample No. 5, and these crosslinked forms were irradiated with an electron beam at 15 kGy.

Although crosslinked alginate not containing PGA undergoes shape deformation of the crosslinked form during lyophilization thereby making it difficult to obtain a crosslinked form having a determinate shape, a crosslinked alginate containing PGA is able to be lyophilized while maintaining the shape of the plate into which it is filled, thereby making it possible to enhance production efficiency.

Furthermore, a group that only underwent severing of a nerve branch was evaluated as Sample No. 6, while an intact group that did not undergo severing of a nerve branch was evaluated as Sample No. 7.

Figure 5:
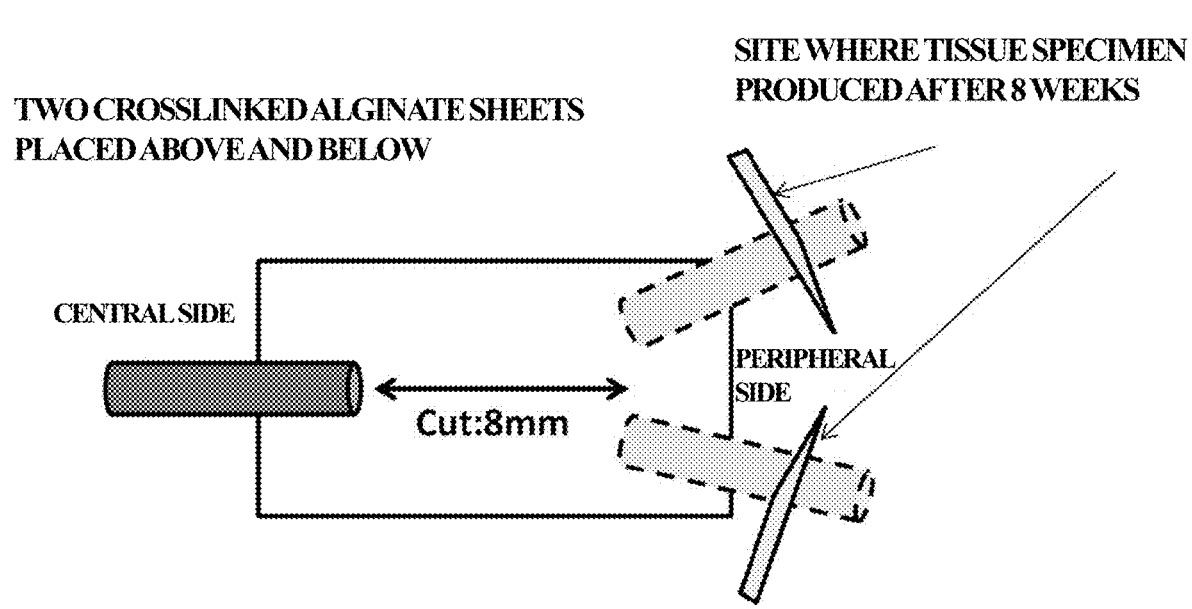
FIG. 5 is a schematic diagram of a test for observing a regeneration inducing effect by applying crosslinked alginate to a defect of a branch of sciatic nerve, and the cylindrical shapes represent nerves and the rectangle represents the crosslinked alginate, and moreover in the example, the crosslinked alginate is placed so as to interpose the severed site of the nerve with two crosslinked alginate sheets.
Figure 6:
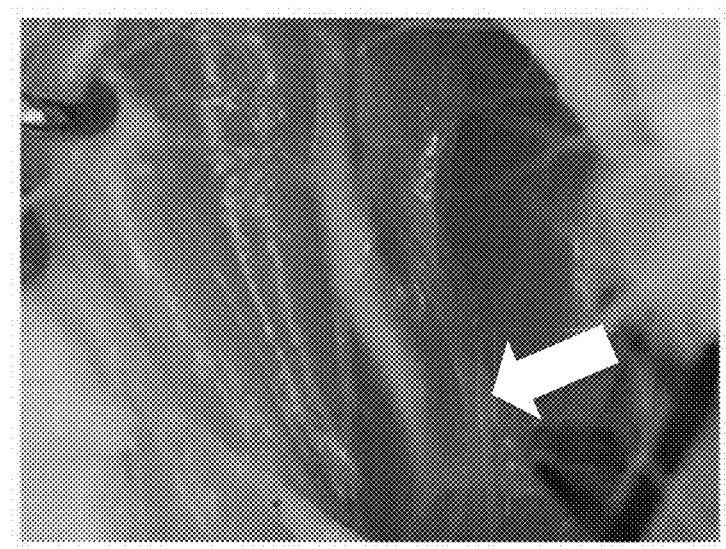
FIG. 6 is a photograph taken 8 weeks after having applied crosslinked alginate A-2EDA (Sample No. 1) to a defect in a branch of sciatic nerve, and the arrow indicates a location where the regenerated axon is excessively thin and not thought to be adequately regenerated.

The number of regenerated axons from the gap to the tibial side and fibula side on the ends was counted for each group followed by calculation of the average values thereof (n=6 to 8). A schematic diagram of a test for applying crosslinked alginate to a defective nerve branch is shown in FIG. 5. In addition, when considering that the average number of regenerated axons in the group having undergone only severing of a nerve branch was 200 on the tibial side and 138 on the fibula side, a number of regenerated axons of 400 or less for both the tibia and fibula in each group was considered to constitute inadequate regeneration, and this was used to determine the percentage of regeneration sites at which regeneration was inadequate in each group. The results are shown in Table 4.

examples of inadequate regeneration, there were also examples in which regenerated nerve became narrower at those sites close to the rat knee. This is thought to be the result of inadequate regeneration caused by pressure being applied to the crosslinked form attributable to movement of the knee, which in turn caused the crosslinked form to tear (rupture) resulting in a loss of continuity of the crosslinked form. Crosslinked alginate containing PGA was suggested to have the potential to demonstrate greater strength, greater resistance to tearing (rupturing) at locations of movement such as the knee, and allow stable exon regeneration in comparison with the crosslinked form not containing PGA. An example of inadequate regeneration in the case of using a crosslinked form not containing PGA (Sample No. 1) is shown in FIG. 6.

In addition, the regeneration effect on a linear nerve gap in week 8 after the procedure was evaluated in compliance with Example 5-(2) for crosslinked alginate not containing PGA (A-2EDA, alginic acid content: 2 mg/cm$^2$) produced in accordance with Example 1-(4) using the low endotoxin sodium alginate of sample A-2 and irradiated with an electron beam at 40 kGy or 60 kGy. As a result, the average numbers of regenerated axons was low at an average of 267 and an average of 275, respectively. The crosslinked forms were not observed to remain at the affected area in week 8

TABLE 4

| Sample No. | Alginic acid Type | Alginic acid Content (mg/cm$_2$) | PGA Content (mg/cm$^2$) | Electron beam dose (kGy) | Tibial nerve Average (pieces) | Peroneal nerve Average (pieces) | Inadequate regeneration (%) |
|---|---|---|---|---|---|---|---|
| 1 | A-2EDA | 2 | None | 20 | 1,204 | 986 | 33 |
| 2 | A-2EDA | 2 | 1.5 | 20 | 2,447 | 1,708 | 0 |
| 3 | A-2EDA | 2 | 3.0 | 20 | 1,801 | 868 | 10 |
| 4 | A-3EDA | 2 | 3.0 | 15 | 1,809 | 1,124 | 19 |
| 5 | A-3EDA | 4 | 3.0 | 15 | 2,392 | 990 | 13 |
| 6 | Severed only | | | | 200 | 138 | 88 |
| 7 | Intact | | | | 4,438 | 2,853 | 0 |

As a result, each of Sample Nos. 1 to 5 demonstrated adequate regeneration of nerve axons both the side of the tibia and fibula, and the numbers of regenerated axons were larger in comparison with the group that underwent severing of the nerve branch only of Sample No. 6. Adequate regeneration effects were also determined to have been obtained in week 8 after the procedure when compared with the sham group (Sample No. 7) that did not undergo severing of the nerve branch.

In addition, there was no significant difference observed between the number of regenerated axons of the crosslinked form not containing PGA (Sample No. 1) and the number of regenerated axons of the crosslinked forms containing PGA (Sample Nos. 2 and 3). On the basis thereof, the presence or absence of PGA in a crosslinked form was indicated not to have a significant effect on nerve regeneration effect. On the other hand, when a comparison was made between each group of the percentage of inadequately regenerated axons for which the number of regenerated axons is 400 or less, in contrast to the crosslinked form not containing PGA (Sample No. 1) demonstrating a value of 33%, the crosslinked forms containing PGA of Sample Nos. 2 to 5 demonstrated values of 0% to 19%. Namely, crosslinked alginate containing PGA was observed to tend to have fewer instances of inadequate regeneration in comparison with crosslinked alginate not containing PGA. Among those after the procedure. When discussing those factors responsible for the lower numbers of regenerated axons in this manner based on previous tests, (i) the crosslinked form containing PGA irradiated with an electron beam at 20 kGy in Example 5-(2) was determined to demonstrate an adequate nerve regeneration effect on a linear nerve gap, and (ii) the presence or absence of PGA in the crosslinked forms was determined to have an effect on the gap of a nerve branch but not have a significant effect on nerve regeneration effect (Table 4), and in consideration thereof, increasing the electron beam dose to 40 kGy or 60 kGy was suggested to have the possibility of affecting nerve regeneration effect.

Example 6 Subcutaneous Implantation Test of Crosslinked Alginate 6-(1) Rat Long-Term Subcutaneous Implantation Test (1)

Since previous tests suggested a correlation between the rate of elimination in the body (residual rate) of crosslinked alginate and nerve regeneration effect, rat subcutaneous implantation tests were carried out on various crosslinked forms to examine the rate of elimination in the body.

Crosslinked alginate produced using the low endotoxin sodium alginate of sample A-2 or A-3 in accordance with Example 1-(4) and Example 5-(1) (including some crosslinked forms that contained PGA) were irradiated with an electron beam while changing the dose to produce samples. The types of samples were as shown in Table 5. Sample Nos. 43 and 44 were samples containing PGA (50 mg/cc, 1.5 mg/cm$^2$) and PLGA (50 mg/cc, 1.5 mg/cm$^2$) only. Each sample having a size measuring 0.7 cm long×1.5 cm wide (without specifying thickness) was implanted beneath the skin on the back of a rat and evaluated histologically four weeks later. Histological evaluations were carried out using specimens prepared in the manner indicated below. Namely, paraffin-embedded blocks were prepared in accordance with ordinary methods followed by staining with hematoxylin-eosin staining and safranin-O staining. Residual of the samples was evaluated by scoring to one of five levels. Namely, the absence of residual sample was scored as 0, a slight amount of residual sample was scored as 1, a small amount of residual sample was scored as 2, a moderate amount of residual sample was scored as 3 and a remarkable amount of residual sample was scored as 4 for each sample, and the average value of n=3 or n=6 for each group was taken to be the residual score of that sample.

The results are shown in Table 5. As a result, crosslinked alginate A-2EDA produced using the low endotoxin sodium alginate of sample A-2 exhibited a trend of decreased residual scores as electron beam dose increased in the crosslinked forms having the same alginate content. In addition, when the alginate content was increased, residual score was observed to tend to increase. Similar trends were observed for crosslinked alginate A-3EDA produced using the low endotoxin sodium alginate of sample A-3. A comparison of A-2EDA and A-3EDA revealed a tendency for the residual score to increase for A-3EDA in comparison with A-2EDA provided the alginate contents and electron beam doses thereof are the same.

TABLE 5

| Sample No. | Alginic acid Type | Content (mg/cm$^2$) | PGA Content (mg/cm$^2$) | PLGA Content (mg/cm$^2$) | Electron beam dose (kGy) | Residual score Average value |
|---|---|---|---|---|---|---|
| 11 | A-2EDA | 2 | | | 0 | 4.0 |
| 12 | A-2EDA | 2 | | | 5 | 3.3 |
| 13 | A-2EDA | 2 | | | 10 | 2.7 |
| 14 | A-2EDA | 2 | | | 15 | 1.5 |
| 15 | A-2EDA | 2 | 1.5 | | 15 | 3.0 |
| 16 | A-2EDA | 2 | 3.0 | | 15 | 3.0 |
| 17 | A-2EDA | 2 | | | 20 | 0 |
| 18 | A-2EDA | 2 | | | 40 | 0 |
| 19 | A-2EDA | 2 | | | 60 | 0 |
| 20 | A-2EDA | 3 | | | 0 | 3.7 |
| 21 | A-2EDA | 3 | | | 20 | 3.0 |
| 22 | A-2EDA | 3 | | | 40 | 0.3 |
| 23 | A-2EDA | 5 | | | 0 | 4.0 |
| 24 | A-2EDA | 5 | | | 20 | 3.3 |
| 25 | A-2EDA | 5 | | | 40 | 4.0 |
| 26 | A-3EDA | 2 | | | 0 | 4.0 |
| 27 | A-3EDA | 2 | | | 5 | 4.0 |
| 28 | A-3EDA | 2 | | | 10 | 4.0 |
| 29 | A-3EDA | 2 | | | 15 | 3.3 |
| 30 | A-3EDA | 2 | 1.5 | | 15 | 3.3 |
| 31 | A-3EDA | 2 | 3.0 | | 15 | 4.0 |
| 32 | A-3EDA | 2 | | | 20 | 3.0 |
| 33 | A-3EDA | 2 | | | 40 | 0.0 |
| 34 | A-3EDA | 2 | | | 60 | 0.3 |
| 35 | A-3EDA | 3 | | | 0 | 4.0 |
| 36 | A-3EDA | 3 | | | 20 | 3.7 |
| 37 | A-3EDA | 3 | | | 40 | 0.7 |
| 38 | A-3EDA | 3 | | | 100 | 0 |
| 39 | A-3EDA | 5 | | | 0 | 4.0 |
| 40 | A-3EDA | 5 | | | 20 | 3.7 |
| 41 | A-3EDA | 5 | | | 40 | 1.0 |
| 42 | A-3EDA | 5 | | | 100 | 0 |
| 43 | | | 1.5 | | 0 | 4.0 |
| 44 | | | | 1.5 | 0 | 4.0 |

Example 6-(2) Rat Long-Term Subcutaneous Implantation Test (2)

Samples were prepared as shown in Table 6 in accordance with Example 1-(4) and Example 5-(1) and implanted beneath the skin on the back of rats in the same manner as Example 6-(1) followed by histologically evaluating residual sample after 8 and 12 weeks. Histological evaluations were carried out using samples prepared in the following manner. Namely, after retrieving the implanted subcutaneous tissue and fixing with 10% neutral buffered formalin solution, the tissue was cut out to prepare paraffin-embedded blocks followed by hematoxylin-eosin staining and safranin-O staining. Residual sample was evaluated by scoring to one of five levels. Namely, the absence of residual sample was scored as 0, a slight amount of residual sample was scored as 1, a small amount of residual sample was scored as 2, a moderate amount of residual sample was scored as 3 and a remarkable amount of residual sample was scored as 4 for each sample, and the average value of n=3 for each group was taken to be the residual score of that sample.

TABLE 6

| Sample No. | Alginic acid Type | Content (mg/cm$^2$) | PGA Content (mg/cm$^2$) | Electron beam dose (kGy) | Residual score (average value) 8 weeks | 12 weeks |
|---|---|---|---|---|---|---|
| 51 | A-3EDA | 2 | 0 | 15 | 2 | 0.7 |
| 52 | A-3EDA | 2 | 3.0 | 15 | 1.7 | 0 |
| 53 | A-3EDA | 4 | 3.0 | 15 | 4 | 3.3 |
| 54 | A-3EDA | 2 | 3.0 | 20 | 1.7 | 0.7 |
| 55 | A-3EDA | 4 | 3.0 | 20 | 3 | 1.3 |
| 56 | A-3EDA | 2 | 3.0 | 30 | 1 | 0.3 |

As a result, the residual scores of each sample gradually decreased after 8 and 12 weeks. The addition of PGA was thought not to have a large effect on residual rate based on a comparison of the residual rates of Sample Nos. 51 and 52. In addition, increasing the content of alginate was indicated to cause an increase in sample residual rates based on a comparison of Sample Nos. 52 and 53. Sample Nos. 52 and 53 are crosslinked forms for which nerve regeneration effects were confirmed as Sample Nos. 4 and 5 in Table 4, while Sample No. 54 is a crosslinked form for which nerve regeneration effects were confirmed in Example 5-(3). In this manner, when a subcutaneous implant test was carried out on the backs of rats using the nerve regeneration-inducing material, confirmation of residual sample was also thought to be one of the desirable factors for nerve regeneration effect based on a histological evaluation of the affected area at 8 and 12 weeks after implant.

Example 7 Water Degradation Test of Crosslinked Alginate

Degradation of Crosslinked Alginate was Evaluated by an In Vitro Test.

Four samples cut to a size of 1 cm long×1 cm wide (without specifying thickness) were placed in a 50 mL volume centrifuge tube (glass) followed by adding 25 mL of physiological saline, shaking in a constant-temperature shaking water bath and observing changes in the samples over time. The longitudinal and horizontal cut surfaces of the sample were cut so as to intersect perpendicularly. The thickness of each sample was from about 2 mm to about 8 mm. The measurement times consisted of 4 hours, 1 day (24 hours), 2 days (48 hours), 3 days (72 hours), 4 days (96 hours), 5 days (120 hours) and 6 days (144 hours) after the start of testing. The samples were weighed prior to the start of testing. After vacuum-filtering the liquid obtained after measurement with a membrane filter having a pore diameter of 10 µm (Omnipore, Merck KGaA) at each measurement time, images of the filtered residue were acquired followed by drying under reduced pressure (60° C.) to a constant weight. The remaining samples were weighed and the ratio of that sample weight to the sample weight prior to the start of testing was calculated as the residual rate (%) of the sample.

The shaking rate of the constant-temperature shaking water bath (Model T-N22S, Thomas Kagaku Co., Ltd., temperature control: CTA401S, Yamato Scientific Co., Ltd.) was set at 120 reciprocations/min. The solvent temperature was set to 50° C. as the set temperature of the constant-temperature shaking water bath.

Sample Nos. 61 to 64, for which nerve regeneration effects were confirmed in rats in Examples 5-(3) and 5-(4), and a crosslinked form not irradiated with an electron beam were evaluated. The evaluated crosslinked forms are shown in Table 7. Sample No. 66 is the same as the crosslinked form obtained in the rat testing of Example 4-(2) that was used after sterilizing with ethanol. A crosslinked form similarly produced using PLGA (50 mg/cc, 1.5 mg/cm$^2$) instead of PGA in compliance with Example 5-(1) was used for Sample No. 68.

TABLE 7

| Sample No. | Alginic acid Type | Alginic acid Content (mg/cm$^2$) | PGA Content (mg/cm$^2$) | PLGA Content (mg/cm$^2$) | Electron beam dose (kGy) |
|---|---|---|---|---|---|
| 61 | A-3EDA | 2 | 1.5 | | 20 |
| 62 | A-3EDA | 2 | 3.0 | | 20 |
| 63 | A-3EDA | 2 | 3.0 | | 15 |
| 64 | A-3EDA | 4 | 3.0 | | 15 |
| 65 | A-3EDA | 2 | | | 0 |
| 66 | A-3EDA | 3 | | | 0 |
| 67 | A-3EDA | 2 | 1.5 | | 0 |
| 68 | A-3EDA | 2 | | 1.5 | 0 |

Figure 7:
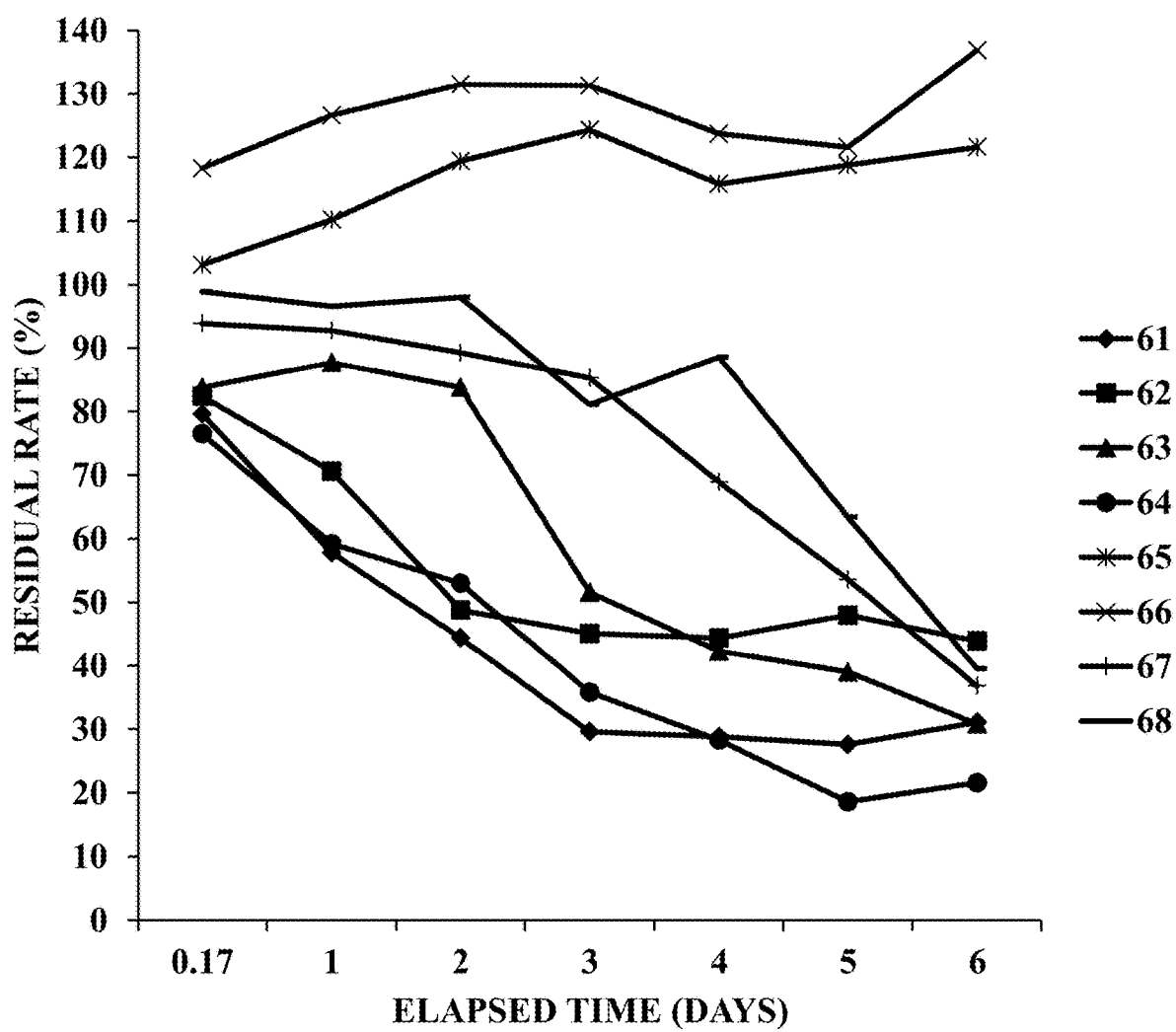
FIG. 7 is a graph indicating the results of evaluating biodegradability of crosslinked alginate in an in vitro test.

The results are shown in FIG. 7. As a result, the crosslinked forms of Sample Nos. 61 to 64 tended to exhibit a decrease in residual rate over time, and residual rates 3 days (72 hours) after the start of testing demonstrated a range of about 20% to about 70%. On the other hand, Sample Nos. 65 and 66, which did not contain PGA and were not irradiated with an electron beam, demonstrated increases in the residual rates thereof. Although Sample Nos. 67 and 68, which contained PGA or PLGA and were not irradiated with an electron beam, were observed to demonstrate decreases in residual rate over time, residual rates 3 days (72 hours) after testing were 80% or higher.

On the basis of the above, in this test, crosslinked forms for which residual rate 3 days (72 hours) after the start of testing was within the range of about 20% to about 80% were suggested to be preferable for nerve regeneration.

Crosslinked forms were similarly evaluated after irradiating while changing the dose of the electron beam or gamma rays. The evaluated crosslinked forms were as shown in Table 8. Sample No. 71 is a crosslinked form for which nerve regeneration effects in rat were confirmed in Example 5-(4).

TABLE 8

| Sample No. | Alginic acid Type | Alginic acid Content (mg/cm$^2$) | PGA Content (mg/cm$^2$) | Electron beam dose (kGy) | Gamma ray dose (kGy) |
|---|---|---|---|---|---|
| 71 | A-3EDA | 2 | 3.0 | 15 | |
| 72 | A-3EDA | 2 | 3.0 | 30 | |
| 73 | A-3EDA | 2 | 3.0 | | 15 |
| 74 | A-3EDA | 2 | 3.0 | | 25 |
| 75 | A-3EDA | 2 | 3.0 | | 50 |

Figure 8:
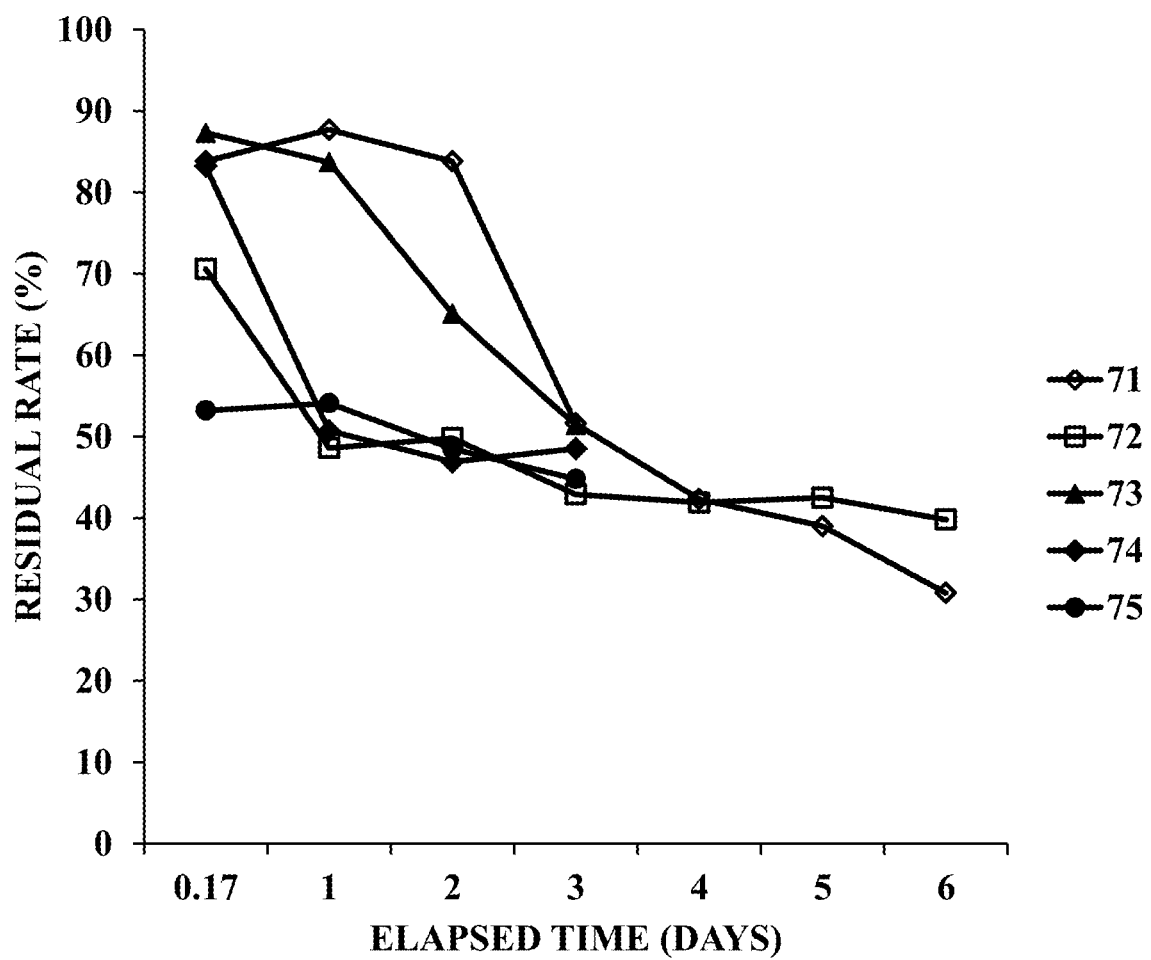
FIG. 8 is a graph indicating the results of evaluating biodegradability of crosslinked alginate in an in vitro test.

The results are shown in FIG. 8. As a result, although Sample Nos. 71 and 72, which are crosslinked forms irradiated with an electron beam, similarly tended to demonstrate decreases in residual rates over time, a comparison of the residual rates between the two samples 4 hours immediately after the start of testing revealed that the residual rate of Sample No. 72, which was irradiated with an electron beam at 30 kGy, was lower than that of Sample No. 71, which was irradiated with an electron beam at 15 kGy. Sample Nos. 73 to 75, which are crosslinked forms irradiated with gamma rays, tended to demonstrate decreased residual rates over time in the same manner as the crosslinked forms irradiated with an electron beam. In addition, among Sample Nos. 73 to 75, the residual rate of Sample No. 75, irradiated with gamma rays at 50 kGy, at 4 hours immediately after the start of testing decreased by about 50%. On the basis of this result, the electron beam and gamma rays were suggested to cause a decrease in residual rate immediately after the start of testing as a result of increasing the radiation dose thereof. In the case of promoting nerve regeneration by installing a crosslinked form in a gap between nerves, if the crosslinked form is eliminated at an early stage after installation, it is thought to be unable to serve as a scaffold early in nerve regeneration. As was described in Example 5-(4), the reason why the elevated regeneration effects for a linear nerve gap were not demonstrated by crosslinked forms irradiated at an electron beam dose of 40 kGy or 60 kGy is thought to be due to the crosslinked form having been eliminated soon after being installed thereby preventing it from fulfilling the role of a nerve scaffold.

Degradation was similarly compared between crosslinked forms similarly produced in accordance with Example 5-(1) using PLGA (50 mg/cc, 1.5 mg/cm$^2$) instead of PGA and crosslinked forms containing PGA. The evaluated crosslinked forms were as shown in Table 9. In Example 5-(3), Sample No. 84 is a crosslinked form for which nerve regeneration effects were confirmed in Example 5-(3) and Sample No. 85 is a crosslinked form for which nerve regeneration effects were confirmed in Example 5-(4).

TABLE 9

| Sample No. | Alginic acid Type | Alginic acid Content (mg/cm²) | PGA Content (mg/cm²) | PLGA Content (mg/cm²) | Electron beam dose (kGy) |
|---|---|---|---|---|---|
| 81 | A-3EDA | 2 | | 1.5 | 0 |
| 82 | A-3EDA | 2 | | 1.5 | 15 |
| 83 | A-3EDA | 2 | 1.5 | | 0 |
| 84 | A-3EDA | 2 | 1.5 | | 20 |
| 85 | A-3EDA | 2 | 3.0 | | 15 |

Figure 9:
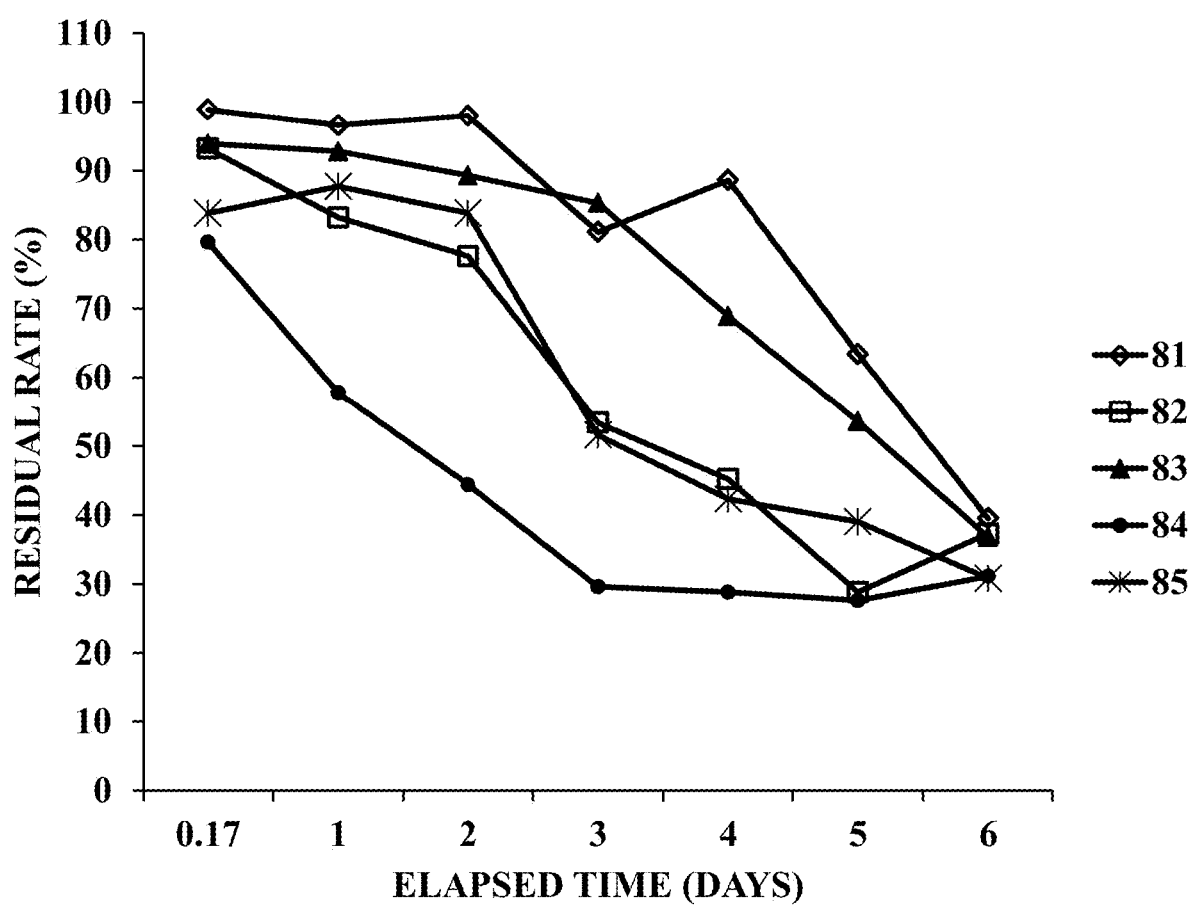
FIG. 9 is a graph indicating the results of evaluating biodegradability of crosslinked alginate in an in vitro test.

The results are shown in FIG. 9. As a result, residual rates of those samples containing PLGA decreased over time in the same manner as samples containing PGA. Sample Nos. 81 and 82 containing PLGA and Sample Nos. 83, 84 and 85 containing PGA tended to demonstrate lower residual rates 4 hours after the start of testing the higher the electron beam dose, after which residual rates were indicated to similarly decrease. In this manner, PLGA was suggested to be able to be used in the same manner as a raw material for crosslinked form instead of PGA.

Example 8 Effect of Crosslinked Form on Normal Human Dermal Fibroblasts

Cell adhesion and cell proliferation of normal human dermal fibroblasts (NHDFs) were compared and evaluated for crosslinked alginates crosslinked with ethylenediamine produced in accordance with Example 1-(4) and commercially available collagen sponges. NHDF and other fibroblasts are thought to obstruct nerve regeneration by migrating to and proliferating in space allocated for nerve regeneration.

The sample groups consisted of (1) A-2EDA, (2) A-3EDA, (3) bovine collagen sponge (SpongeCol (registered trademark), Advanced BioMatrix, Inc.), and (4) 2D control (tissue culture dish). The size of each sample measured about 5 mm long×about 5 mm wide×about 2 mm to about 7 mm thick for sample groups (1) and (2), and diameter of 4 mm×thickness of about 1 mm for sample group (3). $10^4$ cells were disseminated for each sample, and after transferring each sample to a new well in order to separate those cells that were not adhered to the sample after 1 and 4 days of culturing, the number of cells adhered to each sample was evaluated at an absorbance of 450 nm using WST-8 reagent. 10% FCS/EMEM was used for the medium.

Figure 10:
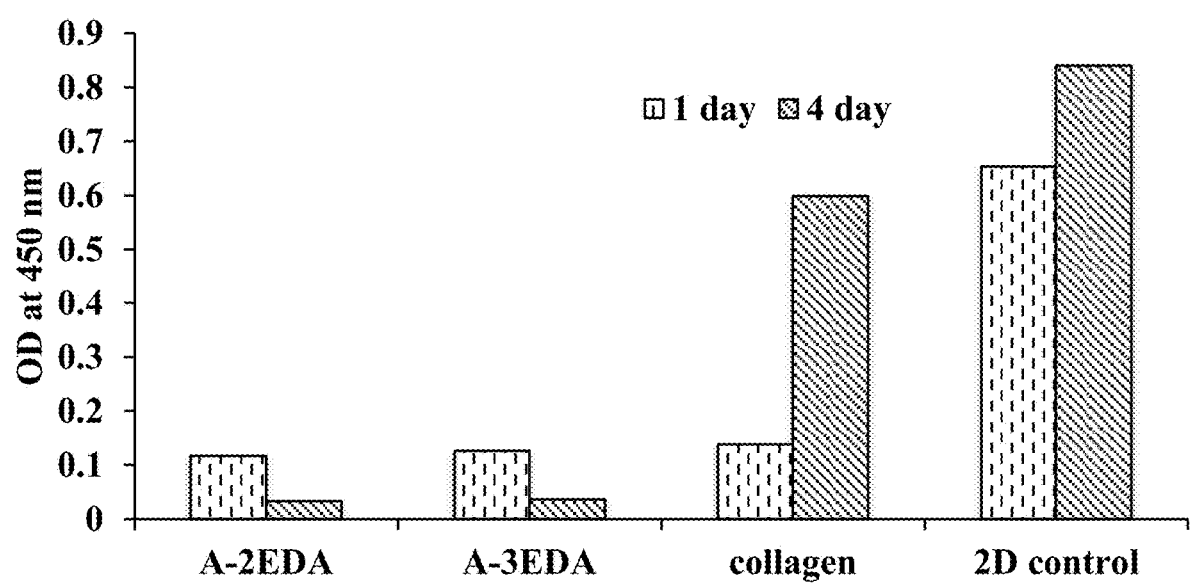
FIG. 10 is a graph indicating the results of evaluating cell adhesion and cell proliferation of non-human dermal fibroblasts (NHDFs).

The results for adhesion and proliferation of the NHDF are shown in FIG. 10. As a result, although the NHDF adhered to the crosslinked forms of A-2EDA and A-3EDA to about the same degree as the collagen sponge in 1 day after culturing, the number of adhered cells subsequently decreased. On the other hand, the collagen sponge was shown to demonstrate an increase in the number of adhered cells. In this manner, crosslinked alginate was shown to inhibit adhesion and proliferation of fibroblasts obstructing nerve regeneration in comparison with collagen sponge.

Example 9 Nerve Regeneration Effect on Rat Cavernous Nerve Plexus Excision Model 9-(1) Production of Rat Cavernous Nerve Plexus Excision Model Rats were immobilized in the supine position under anesthesia induced by inhalation of 2% isoflurane. A midline incision was made in the lower abdomen and the pelvis was expanded under a microscope to expose the pelvic plexus and cavernous nerve. In a treated group and untreated group, the cavernous nerve was secured followed by severing about 2 mm of the cavernous nerve so as to traverse the plexus that was branched in the form of a network. The same procedure was performed on the left and right sides. In the treatment group, crosslinked alginate containing PGA produced in compliance with Example 5-(1) (A-3EDA.PGA100) was sutured and fixed in position by placing so as to adequately cover the stump of the severed nerve. In the untreated group, only the nerve was severed. The cavernous nerve was not severed in a normal control group. Subsequently, the muscle layer and skin of the lower abdomen were sutured. Prior to surgery, benzylpenicillin potassium was injected intramuscularly at a dose of 20,000 units/kg. In addition, 0.01 mg/kg of buprenorphine analgesic was administered subcutaneously at a dose of 1 mL/kg twice a day for 3 days. The number of animals was n=3 per group.

9-(2) Confirmation of Mating Behavior

Three animals of each group were cohabitated with a female confirmed to be in estrus in a cage lined with a metal mesh floor at 4 weeks and 7 weeks after the treatment described in Example 9-(1). On the following day, the presence or absence of mating behavior was confirmed according to the presence or absence of a copulatory plug in the females. Furthermore, those rats for which a copulatory plug was unable to be confirmed were evaluated after continuing observation through day 7.

As a result, the ratios of those rats for which mating behavior was observed (presence of a copulatory plug in females) in the three animals of each group are shown in Table 10. As a result, although mating behavior was observed in 100% of the animals in the normal control group that had not undergone severing of the cavernous nerve, mating behavior was not observed in any animals of the untreated group that underwent severing of the cavernous nerve either after 4 weeks or 7 weeks. On the other hand, mating behavior was observed in 2 of 3 animals of the treatment group in which the above-mentioned crosslinked alginate was placed after severing the cavernous nerve both after 4 weeks and 7 weeks. On the basis thereof, the crosslinked form containing alginate was shown to induce regeneration of a damaged site of the cavernous nerve, in which nerve plexus per se having a network structure was severed at the early stage of 4 weeks after surgery, and enable function to be recovered to a degree that the animals were able to engage in normal mating behavior.

TABLE 10

| Group | Ratio of presence of copulatory plug After 4 weeks | Ratio of presence of copulatory plug After 7 weeks |
|---|---|---|
| Normal control group | 3/3 | 3/3 |
| Untreated group | 0/3 | 0/3 |
| Treated group | 2/3 | 2/3 |

Example 10 Crosslinked Alginate Tear Test

Tensile tear tests were carried out on the six types of crosslinked alginates of Table 11 based on the assumption of suturing the crosslinked form during surgery and the strength of each sample was compared.

Sample Nos. 101 and 104 were crosslinked alginates not containing PGA while the other samples consisted of crosslinked alginates containing PGA, and these were respectively produced in accordance with that described in Example 1-(4) and Example 5-(1). Sample Nos. 101 to 103 were not irradiated with an electron beam while Sample Nos. 104 to 106 were irradiated with an electron beam at 15 kGy.

Figure 11:
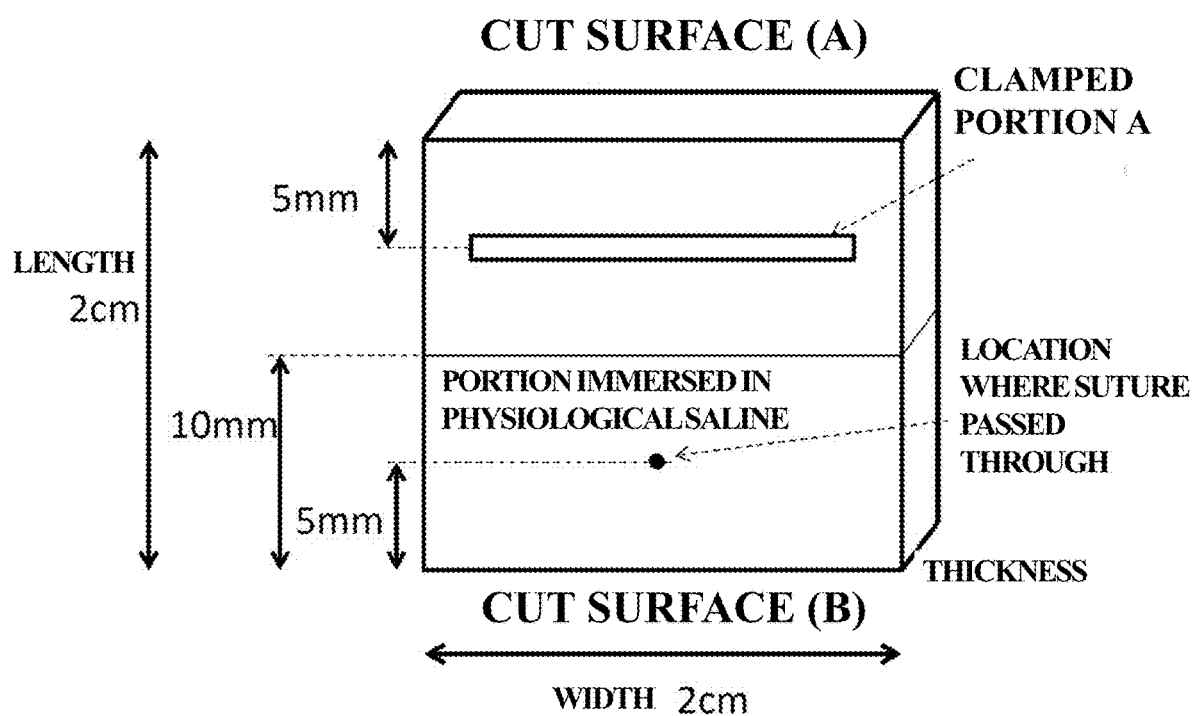
FIG. 11 is a schematic diagram showing the test method of a crosslinked alginate tear test of Example 10.

The test method was as described below. A schematic diagram of the test method is shown in FIG. 11. Each sample was cut to a size of 2 cm long×2 cm wide (without specifying thickness). Here, the longitudinal and horizontal cut surfaces intersected perpendicularly. The thickness of each sample at this time was about 2 mm to about 8 mm. The samples were clamped with a double clip at a location 5 mm away from one of the cut surface with a double clip (having a clamping width of about 15 mm) so as to interpose the same (clamped portion A). An entire region of sample up to 10 mm from the cut surface (B) opposing the clamped portion A was immersed in physiological saline for 15 minutes. A needle with suture (Vicryl (registered trademark), 4-0, SH-1 round needle) was passed through the center of a location 5 mm away from the cut surface (B) of the sample followed by immobilizing both ends of the suture with an instrument. The above-mentioned clamped portion A was pulled at a speed of 10 mm/min horizontal to the square surface of the sample. Pulling was continued until each sample tore in the vicinity of the suture and the load at which the sample was pulled was taken to be the test force. Measurement of tensile load was carried out using a compact physical property testing machine (EZ-Graph, Shimadzu Corporation). Each sample was measured on the basis of n=5 to determine the average value of the maximum point of the test force (maximum test force).

TABLE 11

| Sample No. | Alginic acid Type | Alginic acid Content (mg/cm$^2$) | PGA Content (mg/cm$^2$) | Electron beam (kGy) | Maximum test force average (N) | Standard deviation (N) |
|---|---|---|---|---|---|---|
| 101 | A-3EDA | 2 | None | 0 | 0.094 | 0.017 |
| 102 | A-3EDA | 2 | 3 | 0 | 0.873 | 0.484 |
| 103 | A-3EDA | 4 | 3 | 0 | 0.448 | 0.142 |
| 104 | A-3EDA | 2 | None | 15 | 0.027 | 0.006 |
| 105 | A-3EDA | 2 | 3 | 15 | 0.241 | 0.087 |
| 106 | A-3EDA | 4 | 3 | 15 | 0.196 | 0.118 |

Figure 12:
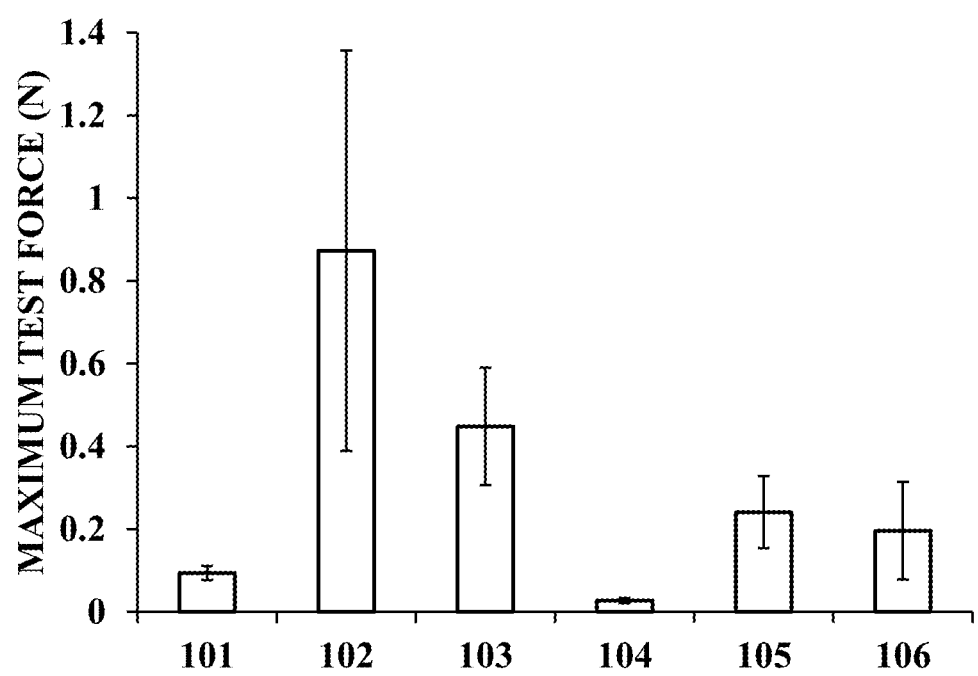
FIG. 12 is a graph indicating the average values of maximum test force (N) when the tensile tear test was carried out for 6 types of crosslinked alginate.

The results are shown in FIG. 12. As a result, among each of the crosslinked forms not irradiated with an electron beam (Sample Nos. 101 to 103) and crosslinked forms irradiated with an electron beam (Sample Nos. 104 to 106), the crosslinked forms containing PGA demonstrated higher maximum test force (N) in comparison with the crosslinked forms not containing PGA. In addition, the crosslinked forms irradiated with an electron beam (Sample Nos. 104 to 106) demonstrated somewhat of a decrease in maximum test force overall in comparison with crosslinked forms not irradiated with an electron beam (Sample Nos. 101 to 103).

Separate from the above, when these crosslinked forms were subjected to a suture test based on the assumption of the suturing technique during surgery and immobilization of the crosslinked form at the installed location, although the crosslinked forms not containing PGA (Sample Nos. 101 and 104) resulted in tearing of the crosslinked form when the suture was tied tightly thereby preventing suturing, Sample Nos. 102, 103, 105 and 106 containing PGA had sufficient strength for enabling suturing. As a result of the tear test, there were no large differences observed between an alginate content of 2 mg/cm$^2$ and 4 mg/cm$^2$, and the results of the tear test and suture test were considered to be largely exclusively dependent on the presence or absence of PGA. On the basis thereof, a crosslinked form having a test force in excess of 0.10 (N) in the above-mentioned test was thought to be desirable for use as a crosslinked form that allows suturing.

The invention claimed is:

1. A method for regenerating a damaged site of a nerve, comprising applying to a damaged site of a nerve of a subject in need thereof a nerve regeneration-inducing material, which is a non-tubular material and which comprises: (A) a crosslinked form obtained by covalent bond crosslinking a low endotoxin bioabsorbable polysaccharide having a carboxyl group within a molecule thereof with at least one type of crosslinking reagent selected from a compound represented by the following general formula (I) and a salt thereof; and (B) a bioabsorbable polymer:

$$R^1HN—(CH_2)_n—NHR^2 \quad (I)$$

wherein, $R^1$ and $R^2$ respectively and independently represent a hydrogen atom or group represented by the formula: —COCH(NH$_2$)—(CH$_2$)$_4$—NH$_2$, and n represents an integer of 2 to 18.

2. The method of claim 1, wherein the bioabsorbable polysaccharide comprises a carboxyl group in a molecule thereof is at least one type selected from the group consisting of alginic acid, an ester thereof and a salt thereof.

3. The method of claim 1, wherein the crosslinking reagent is an N-hydroxysuccinimide salt of the compound represented by general formula (I).

4. The method of claim 3, wherein the N-hydroxysuccinimide salt of the compound represented by general formula (I) is at least one type selected from the group consisting of a 2N-hydroxysuccinimide salt of diaminoethane, a 2N-hydroxysuccinimide salt of diaminohexane, a 4N-hydroxysuccinimide salt of N,N'-di(lysyl)-diaminoethane and a 3N-hydroxysuccinimide salt of N-(lysyl)-diaminohexane.

5. The method of claim 1, wherein the nerve regeneration-inducing material is in the form of a xerogel.

6. The method of claim 1, wherein the bioabsorbable polymer is at least one type selected from the group consisting of polyglycolic acid, polylactic acid, a copolymer thereof, and polycaprolactone.

7. The method of claim 1, wherein the nerve regeneration-inducing material is irradiated with an electron beam and/or gamma rays at an adsorbed dose of 1 kGy to 100 kGy.

8. The method of claim 1, wherein the material is configured such that, after cutting the material to a size measuring 2 cm long×2 cm wide without specifying thickness, clamping the material at a location 5 mm away from one of cut surfaces with a double clip so as to interpose the same (clamped portion A) and immersing a region up to 10 mm from a cut surface (B) opposing the clamped portion A of the material in physiological saline for 15 minutes, and then a tensile tear test is carried out at a speed of 10 mm/min, with the clamped portion A horizontal to a square surface of the material by passing a needle with a suture through the center of a location 5 mm away from the cut surface (B) of the material and immobilizing both ends of the suture with a clamp, the maximum test force (load) of the material is 0.10 (N) to 10.0 (N).

9. The method of claim 2, wherein the content of at least one type selected from the group consisting of alginic acid, an ester thereof and a salt thereof in the material is 0.2 mg/cm$^2$ to 12 mg/cm$^2$.

10. The method of claim 1, wherein the content of bioabsorbable polymer in the material is 0.05 mg/cm$^2$ to 30 mg/cm$^2$.

11. The method of claim 1, wherein the nerve is a peripheral nerve, a central nerve or a combination thereof.

12. The method of claim 1, wherein the damaged site of the nerve is a damaged site of a nerve branch, a damaged site of a nerve plexus or a combination thereof.

13. The method of claim 12, wherein the damaged site is present in at least one location selected from the group consisting of the prostate gland, bladder, cavernous body, arm, extremities, brain, spinal cord, face, neck, waist(lumbar region), sacrum, lumbosacrum, genitals, heart, abdominal cavity, lower abdomen, pelvis, within the thoracic cavity and within the intestinal wall.

14. The method of claim 1, wherein the treated subject suffers from nerve damage selected from the group consisting of nerve damage accompanying tumor resection, lymph node dissection and/or trauma, and nerve damage accompanying tissue reconstruction.

\* \* \* \* \*